United States Patent
Ortyn et al.

(10) Patent No.: US 6,563,583 B2
(45) Date of Patent: May 13, 2003

(54) MULTIPASS CAVITY FOR ILLUMINATION AND EXCITATION OF MOVING OBJECTS

(75) Inventors: William E. Ortyn, Bainbridge Island, WA (US); David A. Basiji, Seattle, WA (US)

(73) Assignee: Amnis Corporation, Seattle, WA (US)

( * ) Notice: Subject to any disclaimer, the term of this patent is extended or adjusted under 35 U.S.C. 154(b) by 0 days.

(21) Appl. No.: 09/976,465

(22) Filed: Oct. 12, 2001

(65) Prior Publication Data

US 2002/0057432 A1 May 16, 2002

Related U.S. Application Data

(63) Continuation-in-part of application No. 09/689,172, filed on Oct. 12, 2000.
(60) Provisional application No. 60/240,125, filed on Oct. 12, 2000.

(51) Int. Cl.[7] ............................................... G01B 11/00
(52) U.S. Cl. .................................... 356/400; 356/399
(58) Field of Search ................................. 356/338, 138, 356/399, 400

(56) References Cited

U.S. PATENT DOCUMENTS

| | | | |
|---|---|---|---|
| 3,518,001 A | 6/1970 | Hell | 356/87 |
| 3,572,946 A | 3/1971 | Little | 356/181 |
| 4,311,387 A | 1/1982 | deMey et al. | 356/318 |
| 4,786,165 A | 11/1988 | Yamamoto et al. | 356/23 |
| 4,792,228 A | * 12/1988 | Haffner | 356/138 |
| 4,840,483 A | * 6/1989 | Haffner | 356/153 |
| 4,848,905 A | 7/1989 | Iino | 356/338 |
| 4,906,094 A | 3/1990 | Ashida | 356/336 |
| 5,159,397 A | 10/1992 | Kosaka et al. | 356/73 |
| 5,159,398 A | 10/1992 | Maekawa et al. | 356/73 |
| 5,159,642 A | 10/1992 | Kosaka | 382/6 |
| 5,247,339 A | 9/1993 | Ogino | 356/73 |
| 5,272,354 A | 12/1993 | Kosaka | 250/574 |
| 5,273,633 A | 12/1993 | Wang | 204/180.1 |
| 5,422,712 A | 6/1995 | Ogino | 356/73 |
| 5,444,527 A | 8/1995 | Kosaka | 356/73 |
| 5,471,294 A | 11/1995 | Ogino | 356/73 |

(List continued on next page.)

FOREIGN PATENT DOCUMENTS

WO   WO 00/42412   7/2000   ......... G01N/15/02

OTHER PUBLICATIONS

Ong, S.–H.; Horne, D.; Yeung, C.–K.; Nickolls, P.; Cole, T. "Development of an Image Flow Cytometer." Analytical and Quantitative Cytology and Histology. XIVth International Conference on Medical and Biological Engineering and the VIIth International Conference on Medical Physics, Espoo, Finland. Aug. 11–15, 1985. pp. 375–382.

Ong, Sim Heng. "Development of a System for Imaging and Classifying Biological Cells in a Flow Cytometer." Doctor of Philosophy Thesis. University of Sydney, School of Electrical Engineering. Aug. 1985.

Primary Examiner—Frank G. Font
Assistant Examiner—Roy M Punnoose
(74) Attorney, Agent, or Firm—Ronald M. Anderson

(57) ABSTRACT

A multipass cavity system employs a beam of light that is reflected back and forth between reflective surfaces a plurality of times, illuminating a different portion of the field of view with each pass until the light exits the reflection cavity. The "recycling" of the light beam substantially improves the SNR of the detection system. The present invention is a beam alignment system for use in such a multipass cavity, correcting misalignment in four degrees of freedom; the horizontal and vertical axes, and angle in each of the vertical and horizontal axes. Angular or positional errors lateral to the direction of the beam can dramatically affect performance. The present invention enables the measurement and adjustment of each degree of freedom independently, in order to make beam steering corrections and maintain optical alignment. This is accomplished in an automated, closed-loop feedback control system.

39 Claims, 17 Drawing Sheets

U.S. PATENT DOCUMENTS

| | | | |
|---|---|---|---|
| 5,485,276 A | 1/1996 | Bien et al. | 356/437 |
| 5,548,395 A | 8/1996 | Kosaka | 356/73 |
| 5,596,401 A | 1/1997 | Kusuzawa | 356/23 |
| 5,633,503 A | 5/1997 | Kosaka | 250/458.1 |
| 5,644,388 A | 7/1997 | Maekawa et al. | 356/73 |
| 5,644,402 A | 7/1997 | Chevallet | 356/440 |
| 5,674,743 A | 10/1997 | Ulmer | 435/287.2 |
| 5,766,957 A | 6/1998 | Robinson et al. | 436/165 |
| RE35,868 E | 8/1998 | Kosaka | 250/574 |
| 5,831,723 A | 11/1998 | Kubota et al. | 356/73 |
| 5,854,685 A | 12/1998 | Levine | 356/440 |
| 6,256,096 B1 | 7/2001 | Johnson | 356/335 |

\* cited by examiner

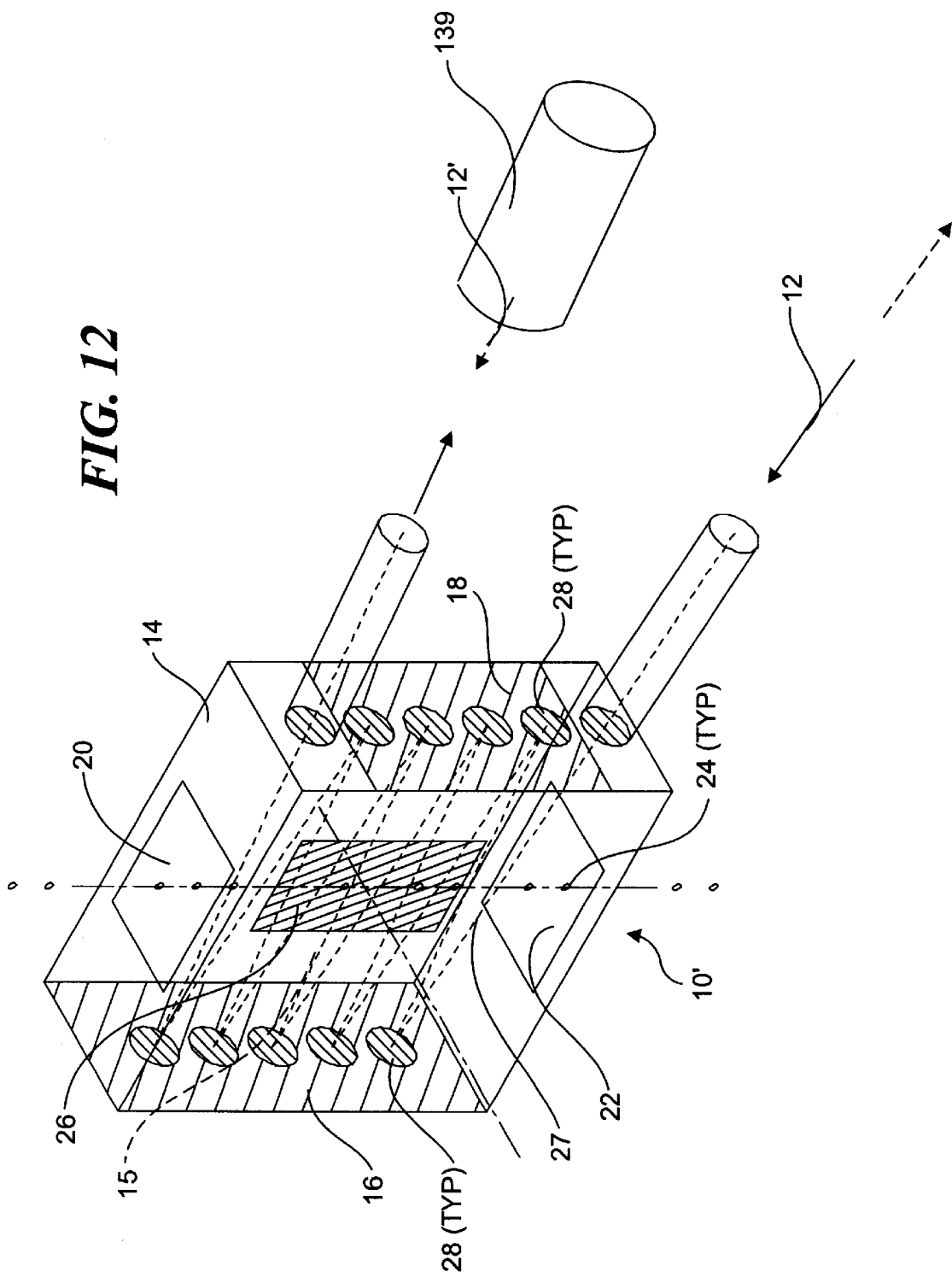

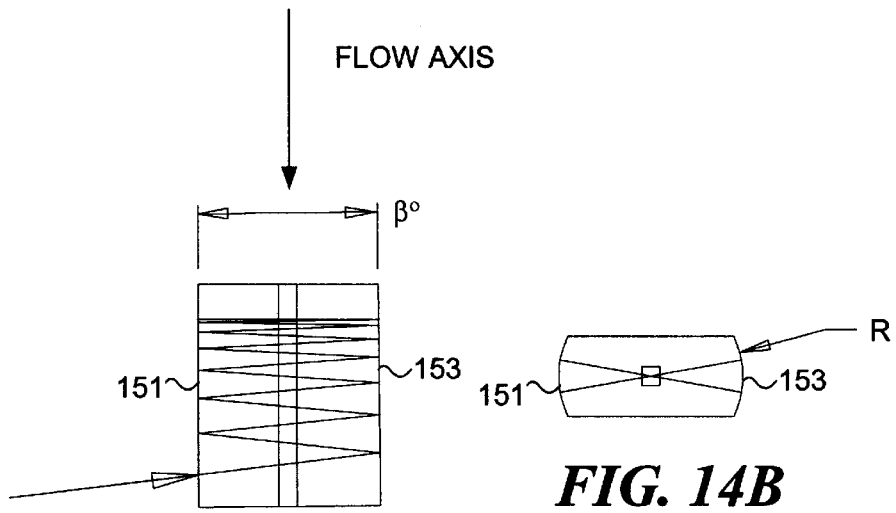
FIG. 14A
FIG. 14B
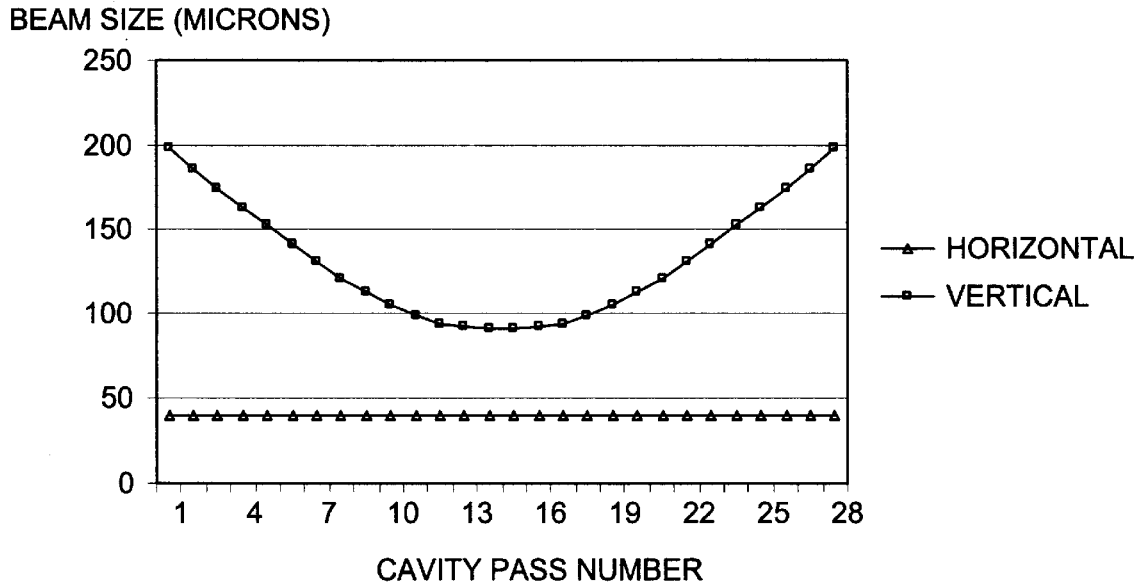
FIG. 15

MULTIPASS CAVITY FOR ILLUMINATION AND EXCITATION OF MOVING OBJECTS

RELATED APPLICATIONS

This application is a continuation-in-part of U.S. patent application Ser. No. 09/689,172, filed on Oct. 12, 2000 and is also based on provisional application Serial No. 60/240,125, filed on Oct. 12, 2000, the benefits of the filing dates of which are hereby claimed under 35 U.S.C. §§119(e) and 120.

FIELD OF THE INVENTION

This invention generally relates to illumination of moving objects or particles for purposes of analysis and detection, and more specifically, to an apparatus and method for increasing the amount of incident light upon these objects to increase scattered, fluorescent, and other signals from moving objects, such as cells, and for detecting the presence and composition of Fluorescence In-Situ Hybridization (FISH) probes within cells.

BACKGROUND OF THE INVENTION

There are a number of biological and medical applications that are currently impractical due to limitations in cell and particle analysis technology. Examples of such biological applications include battlefield monitoring of known airborne toxins, as well as the monitoring of cultured cells to detect the presence of both known and unknown toxins. Medical applications include non-invasive prenatal genetic testing and routine cancer screening via the detection and analysis of rare cells (i.e., cells with low rates of occurrence) in peripheral blood. All of these applications require an analysis system with the following principal characteristics:

1. the ability to carry out high-speed measurements;
2. the ability to process very large samples;
3. high spectral resolution and bandwidth;
4. good spatial resolution;
5. high sensitivity; and
6. low measurement variation.

In prenatal testing, the target cells are fetal cells that cross the placental barrier into the mother's blood stream. In cancer screening, the target cells are sloughed into the blood stream from nascent cancerous tumors. In either case, the target cells may be present in the blood at concentrations of one to five target cells per billion blood cells. This concentration yields only 20 to 100 cells in a typical 20 ml blood sample. In these applications, as well as others, it is imperative that the signal derived in response to the cells be as strong as possible to provide distinct features with which to discriminate the target cells from other artifacts in the sample.

It would be desirable to increase the amount of light incident upon objects in a sample compared to prior art systems, thereby increasing the signal-to-noise ratio (SNR) of a processing system, improving measurement consistency, and thus, increasing the discrimination abilities of the system. A spectral imaging cell analysis system is described in a pending commonly assigned U.S. Pat. No. 6,249,341 and entitled, "Imaging And Analyzing Parameters Of Small Moving Objects Such As Cells," the drawings and disclosure of which are hereby specifically incorporated herein by reference. This previously filed application describes one approach that is applicable to imaging. It would also be desirable to obtain many of the benefits disclosed in the above-referenced copending application in non-imaging flow cytometers that employ photomultiplier tube (PMT) detectors and any other system that relies on the illumination of objects within a cavity. Depending upon the configuration, substantial benefits should be obtained by increasing the amount of light incident upon an object by as much as a factor of ten or more. Such an increase in the amount of light would enable the use of low power continuous wave (CW) and pulsed lasers in applications that would otherwise require the use of more expensive high power lasers. However, if high power lasers are used for a light source, a processing system should yield higher measurement consistency, higher system throughput, greater illumination uniformity, and other benefits than has been possible with prior systems.

It is a goal in the design of fluorescence instruments to achieve photon-limited performance. When photon-limited performance is achieved, noise sources in the instrument are reduced to insignificance relative to the inherent statistical variation of photon arrivals at the detector. A good example of photon-limited design is found in non-imaging flow cytometers. The PMT detectors employed in these instruments can amplify individual photons thousands of times with very fast rise times.

Non-imaging cytometers take advantage of the PMT's characteristics to achieve photon-limited performance by making the illuminated area as small as possible. Decreasing the laser spot size reduces the amount of time required for an object to traverse a field of view (FOV) of the detectors. The reduced measurement time, in turn, reduces the integrated system noise, but does not reduce the signal strength of the object. The signal strength remains constant because the reduced signal integration time is balanced by the increased laser intensity in the smaller spot. For example, if the FOV in the axis parallel to flow is decreased by a factor of two, an object's exposure time will decrease by a factor of two, but the intensity at any point in that FOV will double, so the integrated photon exposure will remain constant.

The reduced noise and constant signal strength associated with a reduced FOV increases the SNR of the non-imaging cytometer up to a point. Beyond that point, further reductions in the FOV will fail to improve the SNR because the dominant source of variation in the signal becomes the inherently stochastic nature of the signal. Photonic signals behave according to Poisson statistics, implying that the variance of the signal is equal to the mean number of photons. Once photon-limited performance is achieved in an instrument, the only way to significantly improve performance is to increase the number of photons that reach the detector.

A common figure of merit used in flow cytometry is the coefficient of variation (CV), which equals the standard deviation of the signal over many measurements divided by the mean of the signal. Photon noise, as measured by the CV, increases as the mean number of photons decreases. For example, if the mean number of photons in a measurement period is four, the standard deviation will be two photons and the CV will be 50%. If the mean number of photons drops to one, the standard deviation will be one and the CV will be 100%. Therefore, to improve (i.e., decrease) the CV, the mean number of photons detected during the measurement interval must be increased. One way to increase the number of photons striking the detector is to increase photon collection efficiency. If an increase in photon collection efficiency is not possible, an alternative is to increase the number of photons emitted from the object during the measurement interval. Accordingly, it would be beneficial to provide a system in which illumination light incident on an object but not absorbed or scattered is recycled and redirected to strike the object multiple times, thereby increasing photon emission from the object.

In the case of a conventional imaging flow cytometer, such as that disclosed in U.S. Pat. No. 5,644,388, a frame-based charge-coupled device (CCD) detector is used for signal detection as opposed to a PMT. In this system, the field of view along the axis of flow is approximately ten times greater than that in PMT-based flow cytometers. In order to illuminate the larger field of view, the patent discloses a commonly used method of illumination in flow cytometry, in which the incident light is directed at the stream of particles in a direction orthogonal to the optic axis of the light collection system. The method disclosed in the patent differs slightly from conventional illumination in that a highly elliptical laser spot is used, with the longer axis of the ellipse oriented along the axis of flow. As a result of this configuration, the entire FOV can be illuminated with laser light. Given that a laser is used, the intensity profile across the illuminated region has a Gaussian profile along the axis of flow. Therefore, objects at either end of the field of view will have a lower intensity of illumination light. Unlike a non-imaging flow cytometer, the light collection process disclosed in this patent does not continue for the duration of the full traversal of the FOV. Instead, light is collected from objects at specific regions within the FOV. Object movement during the light collection process is limited to less than one pixel by use of a shutter or pulsed illumination source. As a result, the amount of light collected from an object varies as a function of its position in the field of view, thereby increasing measurement variability. In order to partially mitigate this variation, the illumination spot may be sized so that it substantially overfills the FOV to use an area of the Gaussian distribution near the peak where the intensity variation is minimized. However, this approach has the undesired effect of reducing the overall intensity of illumination, or photon flux, by spreading the same amount of laser energy over a significantly larger area. The end result of reducing photon flux is a reduction in the SNR.

Accordingly, it will be apparent that an improved technique is desired to improve the SNR and measurement consistency of an instrument by increasing photon emission from the object and improving the uniformity of illumination. It is expected that such a technique will also have applications outside of cell analysis systems and can be implemented in different configurations to meet the specific requirements of disparate applications of the technology.

SUMMARY OF THE INVENTION

The present invention is directed to correcting beam misalignments in a multipass cavity illumination system that is adapted to increase the amount of signal emitted from an object to increase the SNR and to improve the measurement consistency of devices in which the present invention is applied.

In general, a multipass cavity is formed by the placement of two mirrors on either side of a moving stream of objects. A light collection system is disposed substantially orthogonal to a plane extending through the mirrors and the stream. The light collection system is configured to collect light over a predefined angle and within a predefined region or field of view between the mirrors. Accordingly, the light collection system collects light that is scattered or emitted from objects as they traverse the space between the mirrors. The scattered or emitted light that is collected is directed onto a detector.

A light from a light source is directed through the stream of moving objects in a direction nearly orthogonal to the stream of objects but slightly inclined in the plane that extends through the mirrors and the stream. With cells and most other objects, only a small fraction of the incident light interacts with the objects via absorbance or scatter. The rest of the light passes through the stream, and is then redirected by reflection from a surface back into the stream of moving objects. The light leaves the reflecting surface at a reflected angle that is equal to an incident angle of the light. Due to the reflection angle and the distance between the stream and the first surface, the light intersects the stream on the second pass at a position that is displaced from that at which the light passed though the stream on its initial pass. The light continues through the stream and is redirected by a second surface on the other side of the stream, which is substantially parallel to the first surface, back towards the stream. Again, as a result of the reflection angle and the distance between the second surface and the stream, the light passes through the stream on the third pass at a position that is displaced from that of the second pass. The reflection of the light through the stream continues a plurality of times until the light has traversed a distance along the direction in which the stream is flowing that is substantially equal to the collected field of view of the light collection system. At this point, the light is no longer reflected back through the stream, but is preferably caused to exit the illumination system.

It should be understood that most of the light that passes through the stream is largely unimpeded by the stream or objects in the stream. Therefore, upon subsequent passes, substantial light remains to intercept the object or objects in the stream. By "recycling" light in this manner, the light that would normally be wasted is employed to illuminate the object each time the object passes through the light. Consequently, the SNR of the instrument is substantially improved by increasing the amount of scattered and/or emitted light that is incident on the detector.

Beam misalignment in a multipass cavity has four degrees of freedom, position in the horizontal (X) and vertical (Y) directions and angle in the vertical and horizontal axes, termed tip and tilt respectively. Misalignments in directions along the beam axis or around the beam axis have little affect on the performance of the cavity. However, angular or positional errors lateral to the propagation direction of the beam can dramatically affect performance. The present invention provides apparatus and methods to easily measure and adjust these errors in an independent fashion for each degree of freedom, in order to make beam steering corrections and maintain optical alignment. The present invention of an active cavity beam detection and alignment system allows this to be accomplished in an automated, closed-loop feedback control system.

BRIEF DESCRIPTION OF THE DRAWING FIGURES

The foregoing aspects and many of the attendant advantages of this invention will become more readily appreciated as the same becomes better understood by reference to the following detailed description, when taken in conjunction with the accompanying drawings, wherein:

FIG. 12 is an isometric view of an embodiment of the present invention that employs a retro-reflector to reverse beam traversal, increasing the number of times the beam traverses the flow stream;

Figure 16:
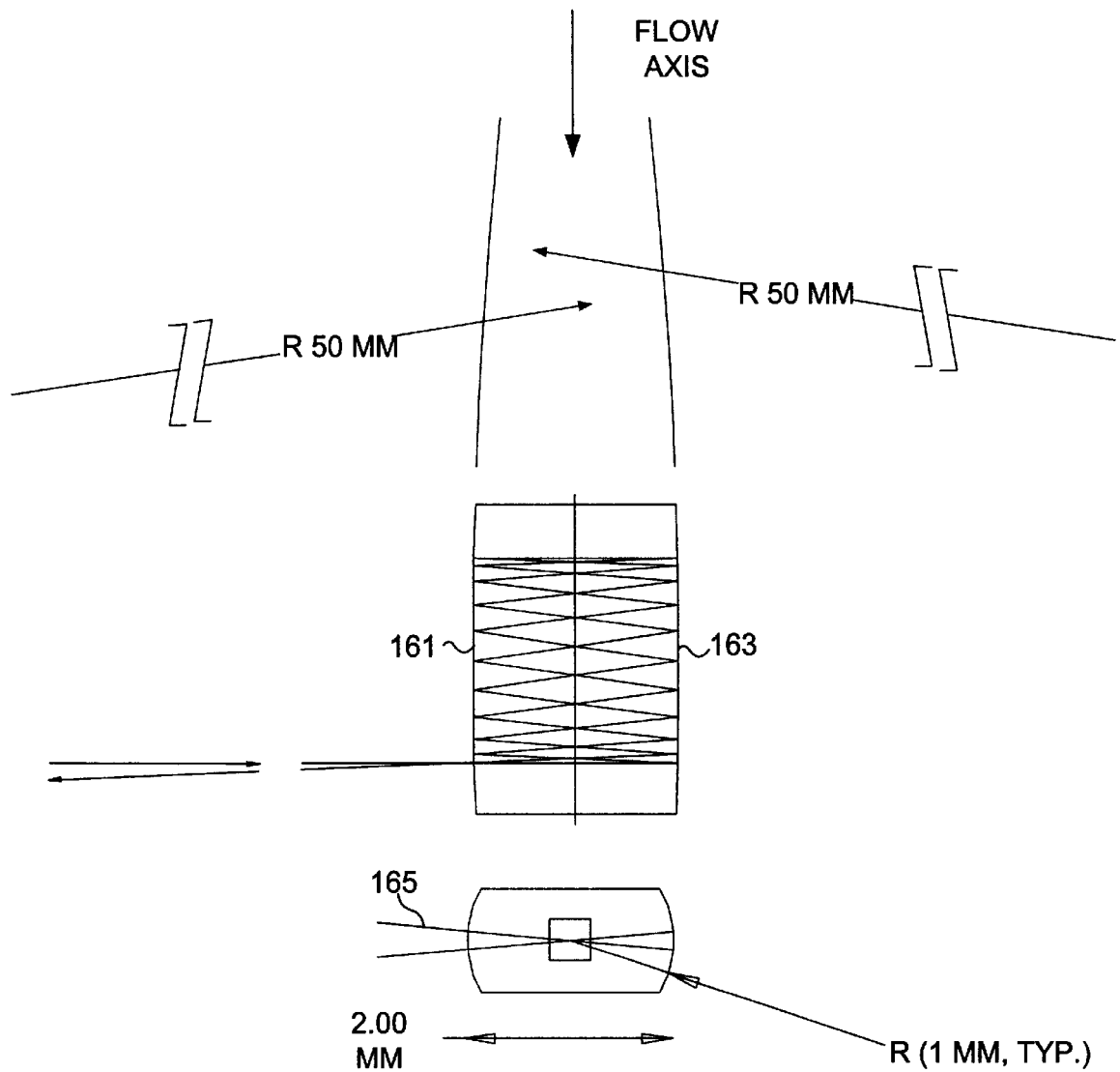
Figure 17:
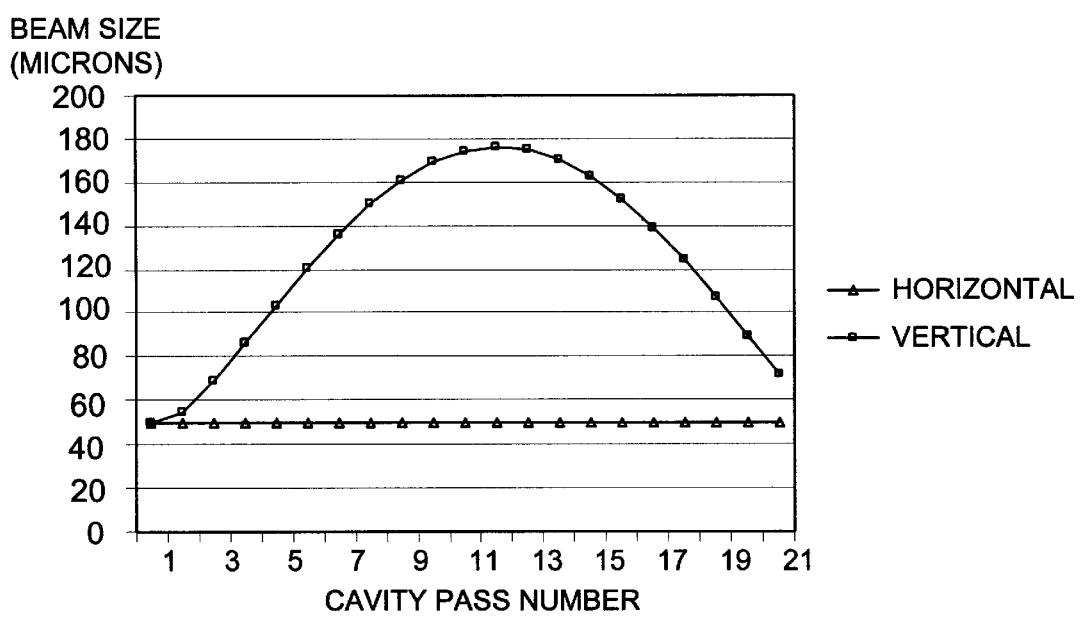
Figure 18:
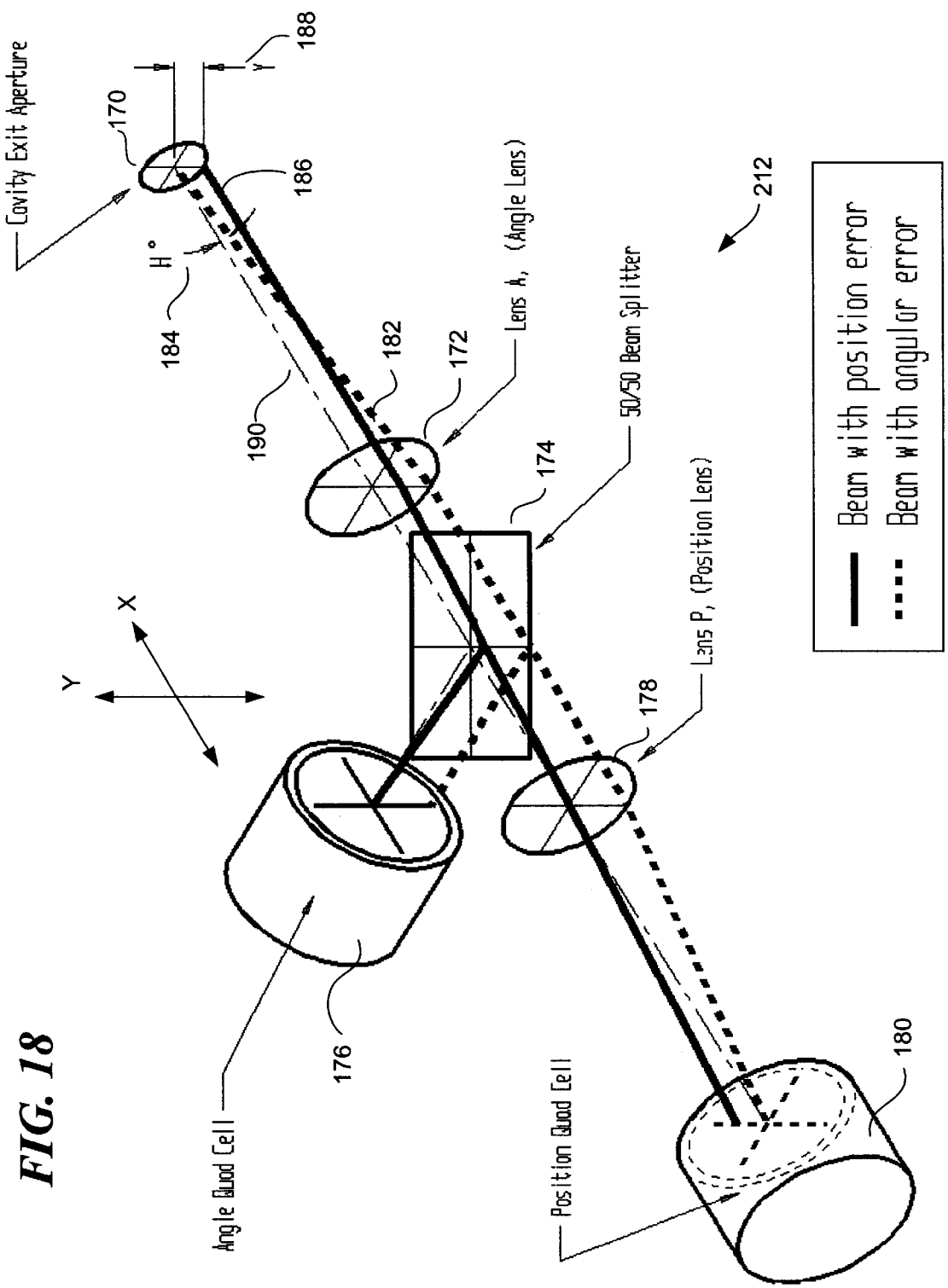
Figure 19A:
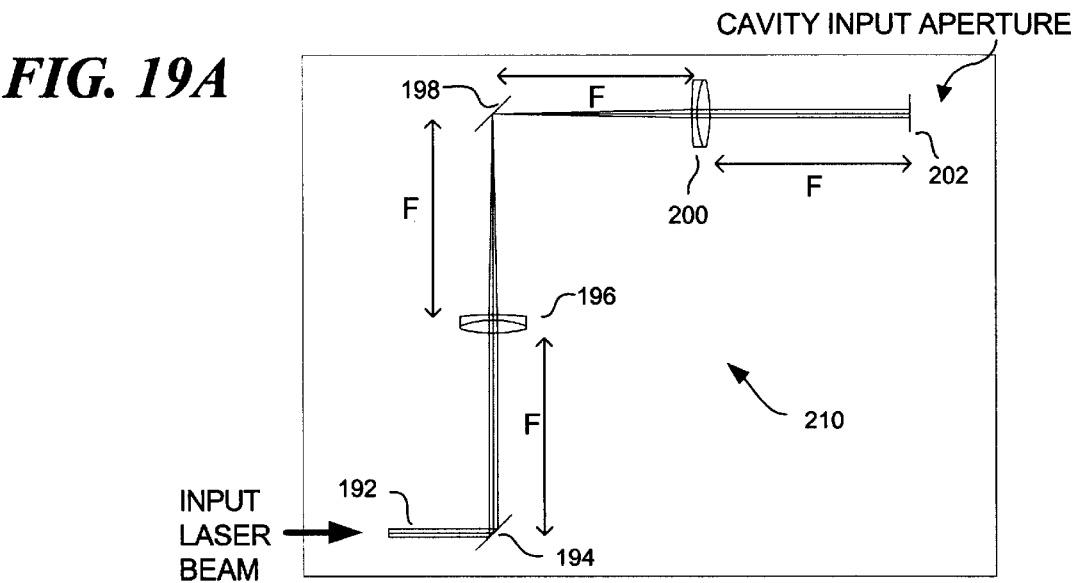
Figure 19B:
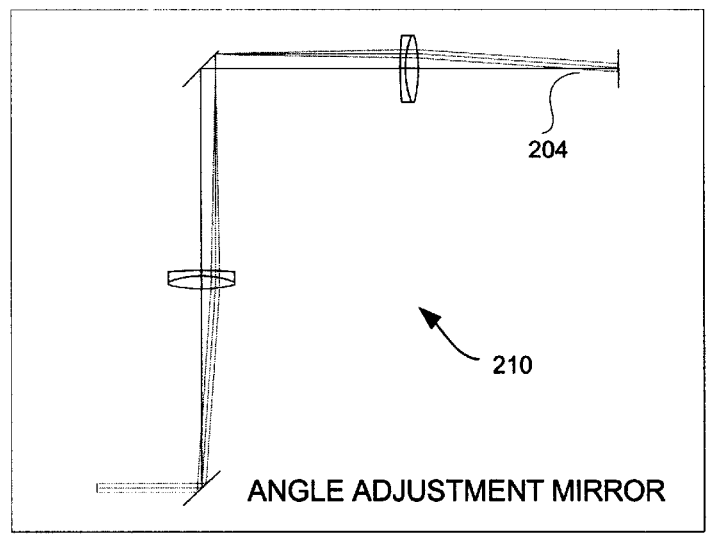
Figure 19C:
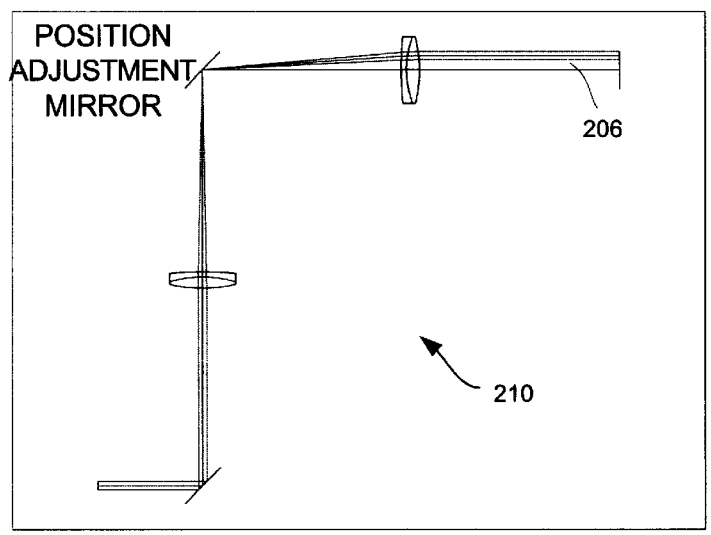
Figure 20:
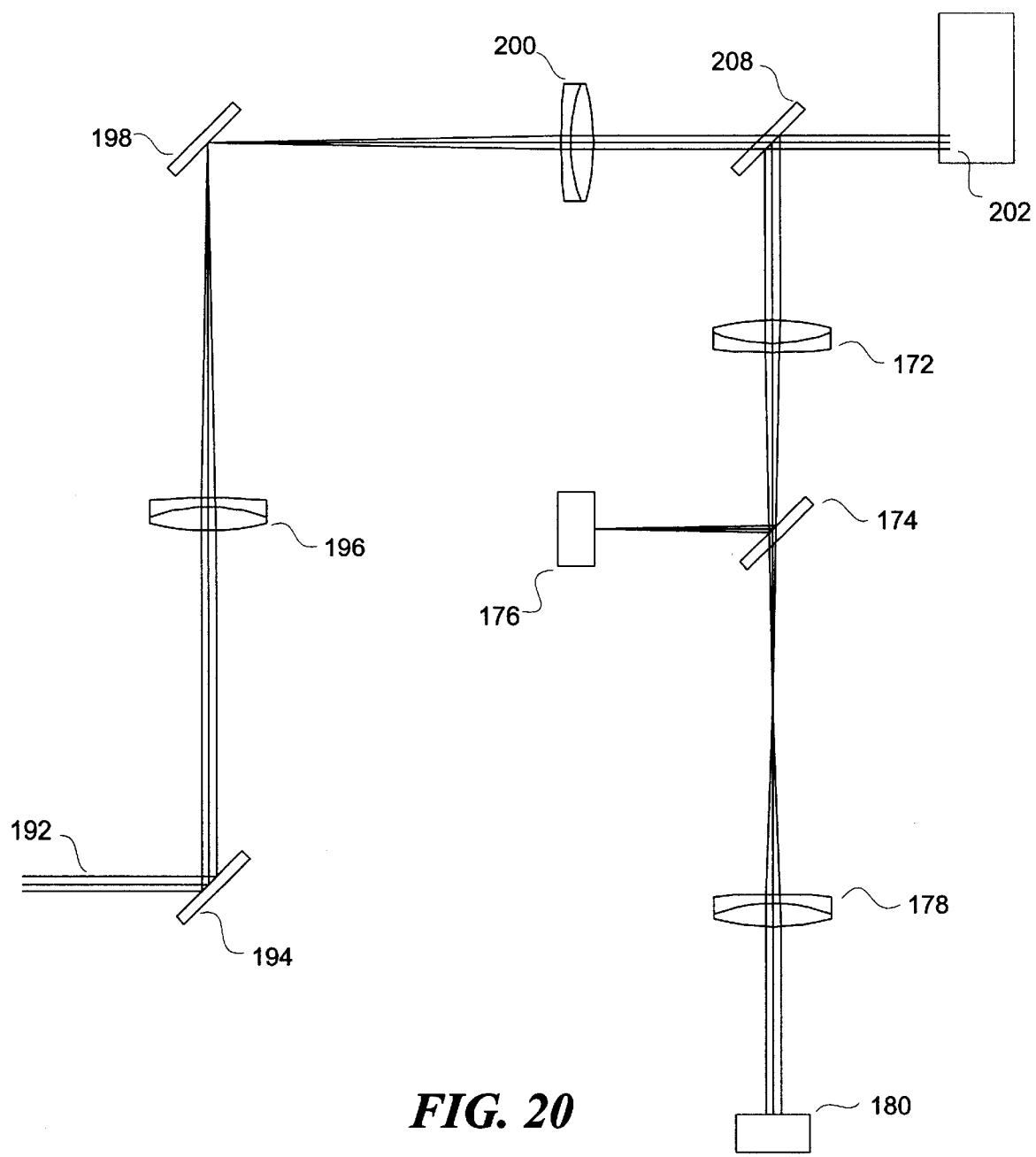
Figure 21:
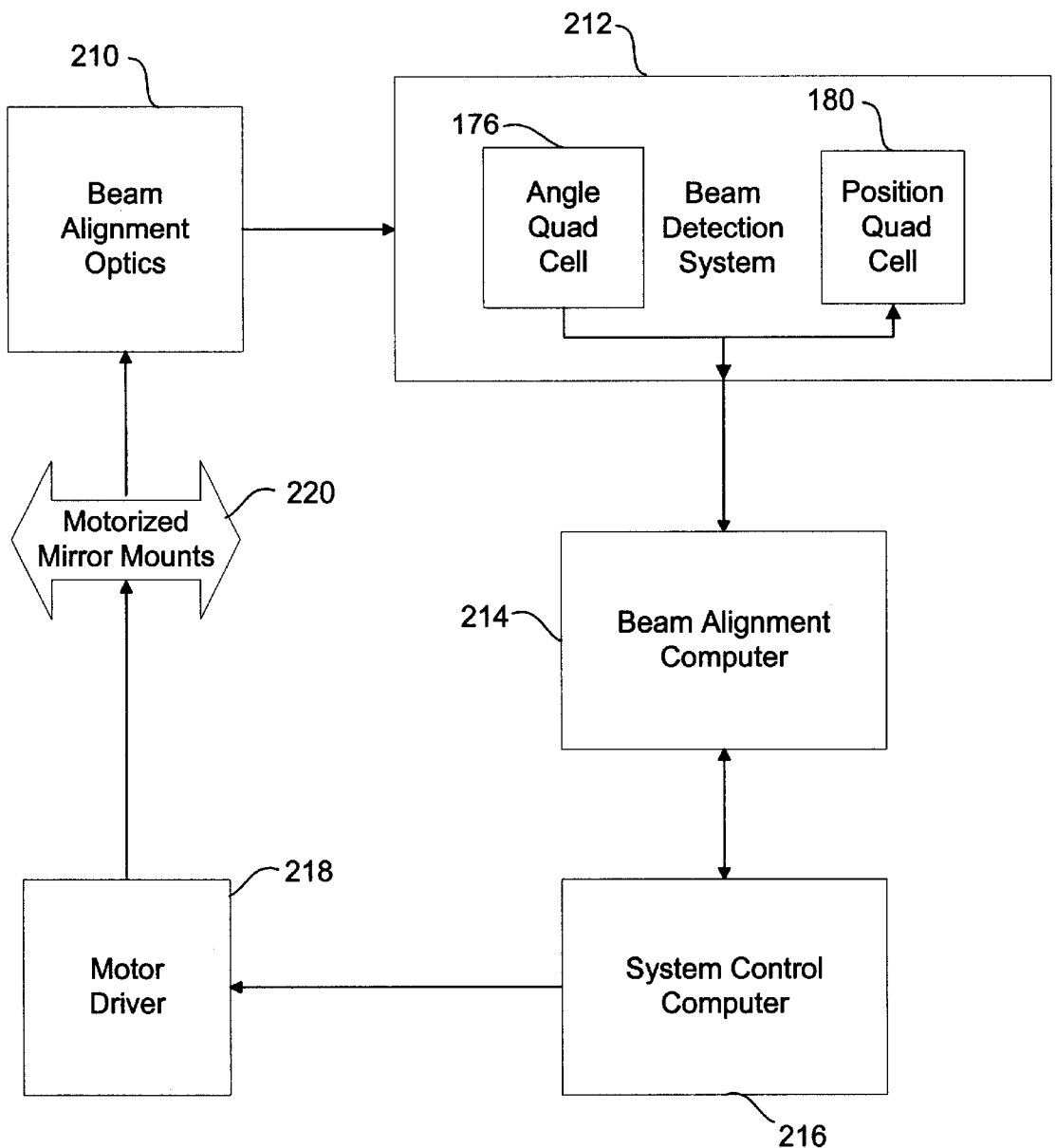
Figure 22:
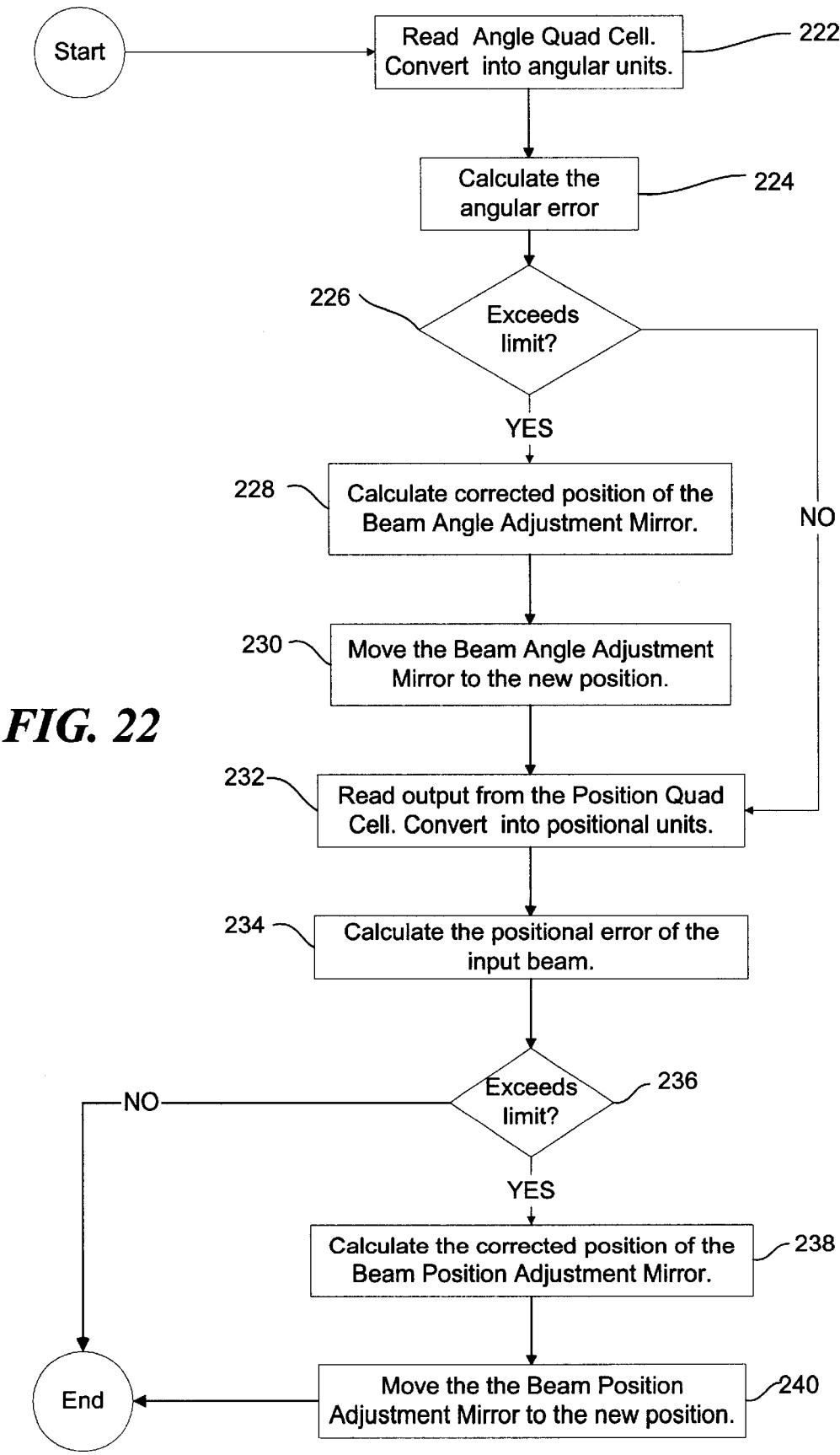
Figure 23:
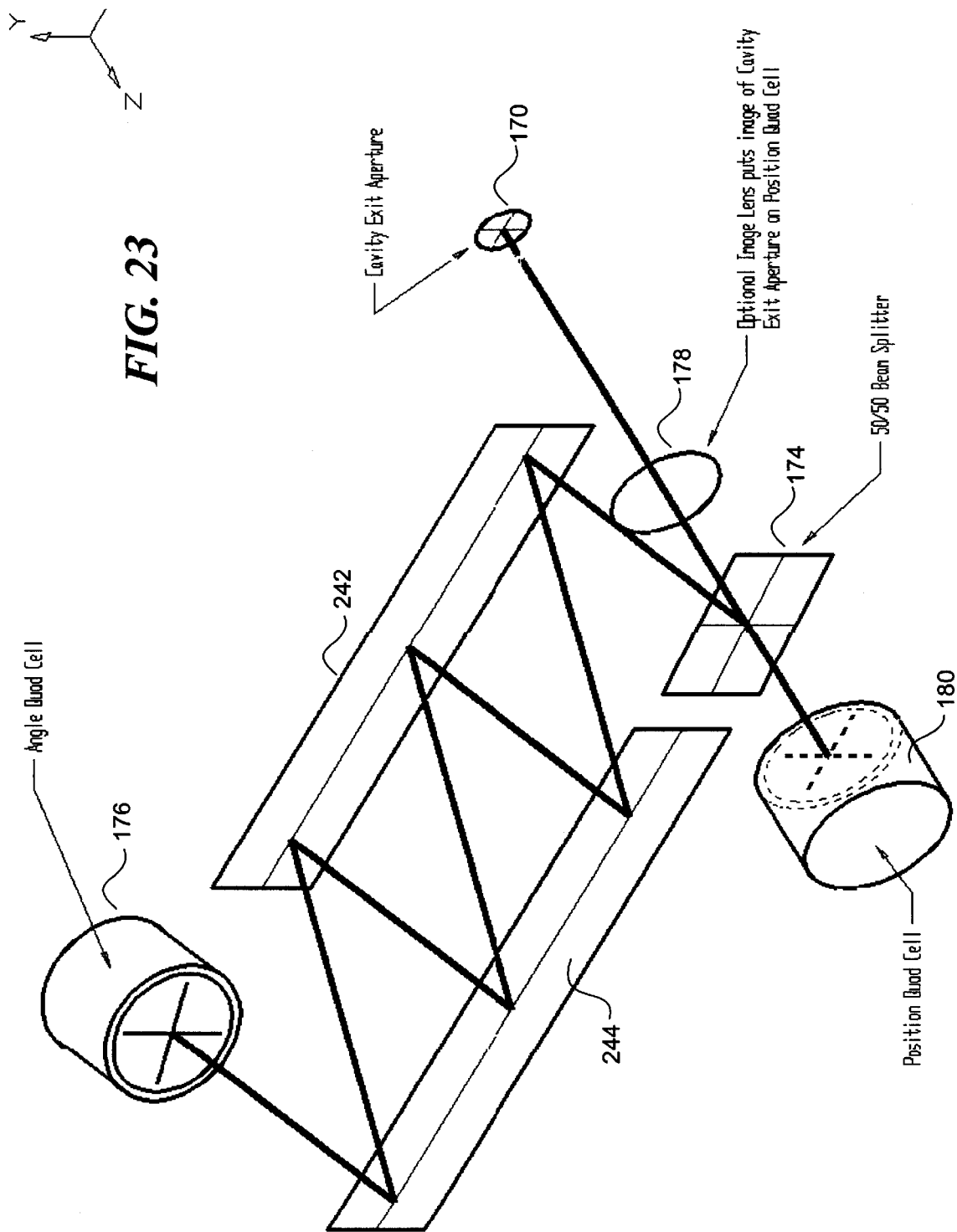

FIGS. 13A–13F schematically illustrate an embodiment of the present invention where the beam traversal direction is reversed after a plurality of passes across the cavity by introducing an angle between the cavity mirrors;

FIGS. 14A–14B further illustrate schematically an embodiment of the present invention wherein the beam traversal direction is reversed after a plurality of passes across the cavity by introducing an angle between the cavity mirrors and in which the mirrors provide an optical power about an axis parallel to the flow axis for refocusing the beam in the horizontal axis with each pass through the cavity;

FIG. 15 is a plot of the beam size in the horizontal and vertical axes for each pass of the beam across the cavity in an embodiment employing 28 passes, as illustrated in FIGS. 14A–14B;

FIG. 16 schematically illustrates an embodiment of the present invention wherein the cavity mirrors have a toroidal surface profile and provide an optical power in both the horizontal and vertical axes for inducing a reversal of beam traversal direction and for refocusing the beam in both axes;

FIG. 17 is a plot of the beam size in the horizontal and vertical axes for each pass of the beam across the cavity in an embodiment employing 21 passes of the beam where the walls of the cavity have the toroidal surface profile illustrated in FIG. 16;

FIG. 18 is an isometric drawing of the beam position and angle detection system used to monitor laser alignment to the cavity in an active cavity alignment embodiment;

FIGS. 19A–19C illustrate schematically the optical system used for active cavity alignment of the input laser beam;

FIG. 20 is a plan view of an optical system for active cavity alignment of the input laser beam integrated with the beam detection optical system of FIG. 18;

FIG. 21 is a functional block diagram showing the major components of a closed-loop active cavity alignment system;

FIG. 22 is an algorithm flow diagram illustrating the logic employed in the control system for the active cavity alignment embodiment; and FIG. 23 is an isometric view of an alternate embodiment of the beam position and angle detection system.

DESCRIPTION OF THE PREFERRED EMBODIMENT

The present invention offers considerable advantages over the prior art for illumination of cells and other types of particles in a flow stream. These advantages arise from the recycling of laser light to increase the photon flux incident upon objects in a flow stream. The present invention can also be configured to improve the uniformity of illumination, while at the same time increasing the photon flux incident upon objects, which is expected to enhance the performance of various flow cytometry applications.

Figure 1:
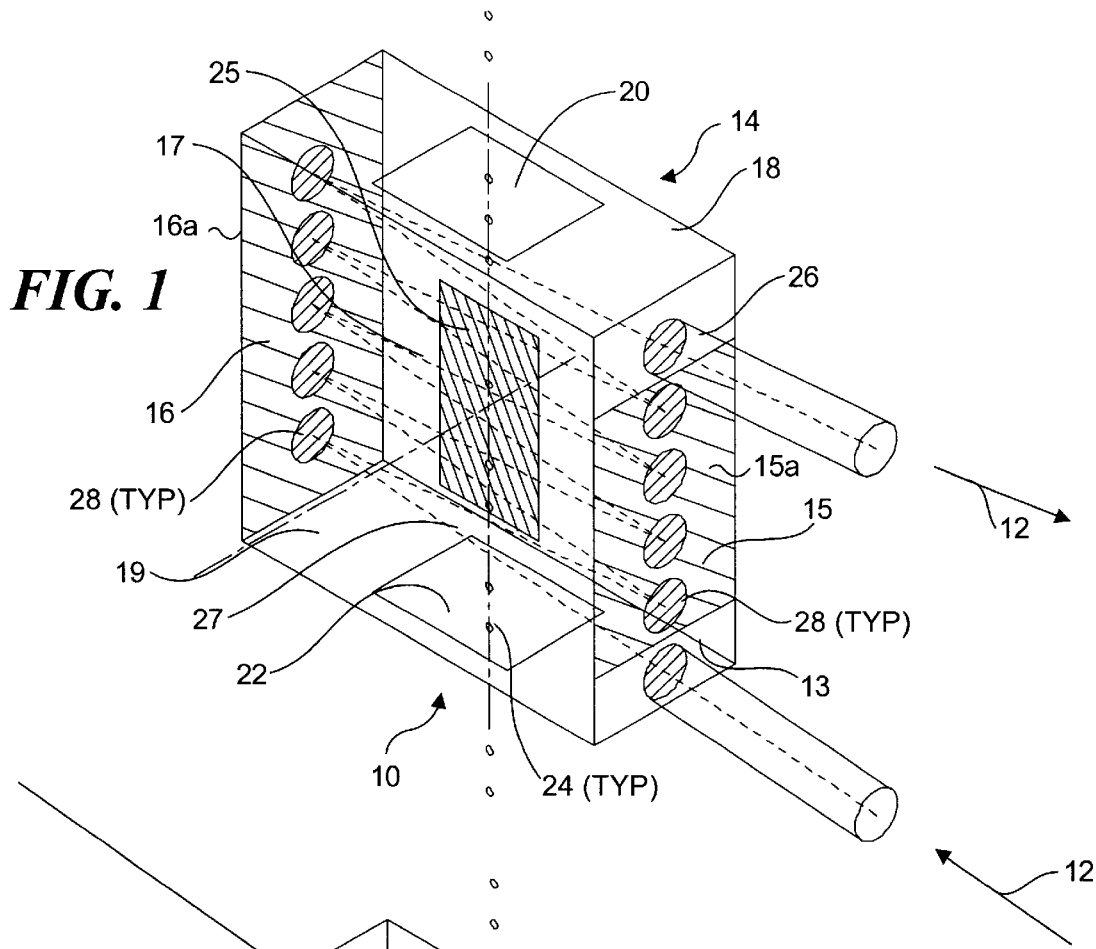
FIG. 1 is an isometric view of an illumination system corresponding to a first embodiment of the present invention.

A first preferred embodiment of an illumination system 10 in accord with the present invention is shown in FIG. 1. Illumination system 10 includes a rectangular solid glass substrate 14 with reflective coatings 15 and 16 applied to two substantially parallel and flat outer surfaces 15a and 16a of the glass substrate. A channel 20 is disposed in the rectangular solid to enable a plurality of objects 24 in a flow stream to pass through illumination system 10 between surfaces 15a and 16a. As is commonly done, the objects may be entrained in a sheath flow (not shown) in order to keep them centered within channel 20. A substantially cylindrical beam of light 12, such as that emitted by a laser source (not shown), is directed toward an uncoated area 13 in surface 15a of the substrate such that a propagation axis of the beam of light (indicated by the arrow) is at a slight angle with respect to a normal to surface 15a. The beam proceeds through surface 15a and passes through at least a portion of the plurality of objects 24 and is then reflected from reflective coating 16 back into the plurality of objects 24. The angle of propagation axis 12a is set such that as beam of light 12 traverses the substrate, it rises a predefined amount, intersecting surface 15a in reflective coating 15 above uncoated area 13. The beam reflects from reflective coating 15 and again passes through the plurality of objects 24.

As objects 24 flow along the channel, corresponding images of the objects are produced with an optical system (not shown in this Figure) having a field of view 25. As shown in FIG. 1, light beam 12 continues to traverse substrate 14 such that it passes through the substrate ten times, thereby illuminating all of field of view 25, before it is allowed to pass out of the substrate through an uncoated area 26 in surface 15a. Reflection spots 28 and dashed lines 27 illustrate the path of the light beam and indicate the points where the beam intersects and reflects from reflective coatings 15 and 16. Reflective coatings 15 and 16 form a reflection cavity 17 through which the plurality of objects 24 pass. Those skilled in the art will appreciate that surfaces 15 and 16 could be independently mounted on their own substrates without the use of the glass substrate 14. By reflecting the light back and forth in this manner, the total amount of light incident on objects 24 is substantially increased over that provided by conventional illumination methods.

Figure 2:
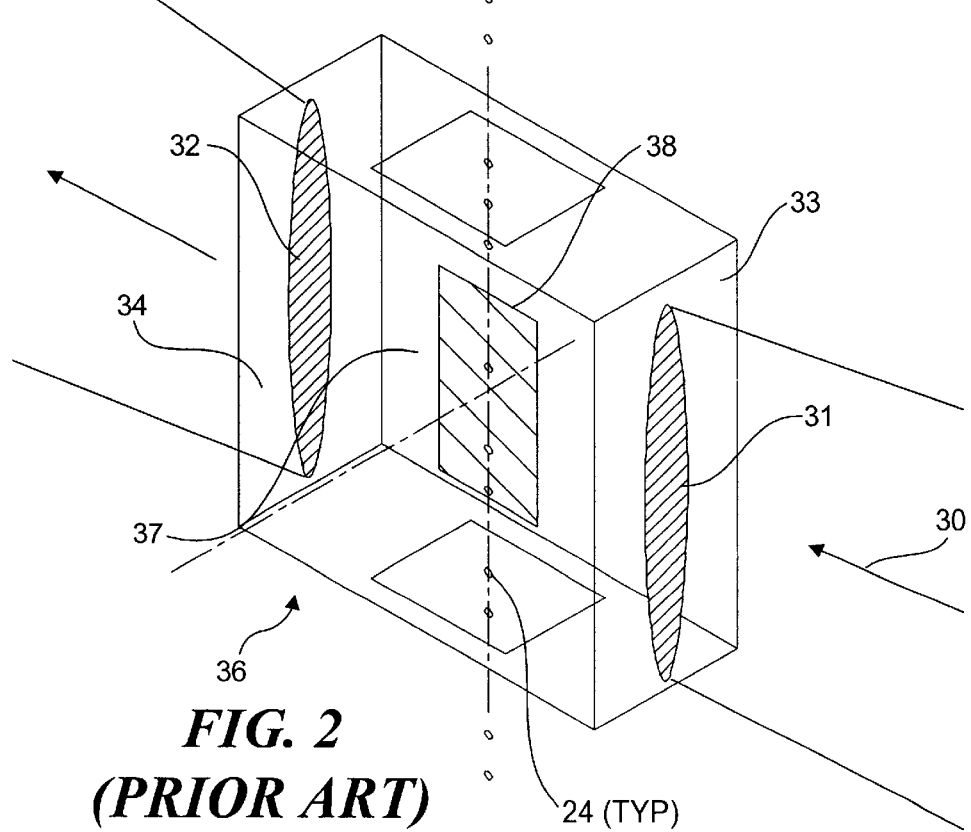
FIG. 2 (Prior Art) is an isometric view of a conventional method for illuminating objects in a flow stream.

In contrast to the foregoing configuration, FIG. 2 illustrates a common approach used in the prior art to illuminate objects in flow cytometers such as those described in U.S.

Pat. No. 5,644,388. In this configuration, an elliptical-shaped beam of light 30 is directed through the substrate 36 and passes through the plurality of objects 24. In order to illuminate all of field of view 38, the light beam size in the flow axis is made substantially larger than that used in the present invention. As a result, the intensity of light at any point in field of view 38 is substantially less than in the present invention, which reduces the amount of light scattered or otherwise emitted from the plurality of objects 24, thereby reducing the SNR of the conventional approaches relative to the SNR of the present invention. Likewise, in the conventional approach, the illumination intensity varies across the field of view in accordance with a Gaussian intensity distribution of the illuminating laser light.

Figure 3:
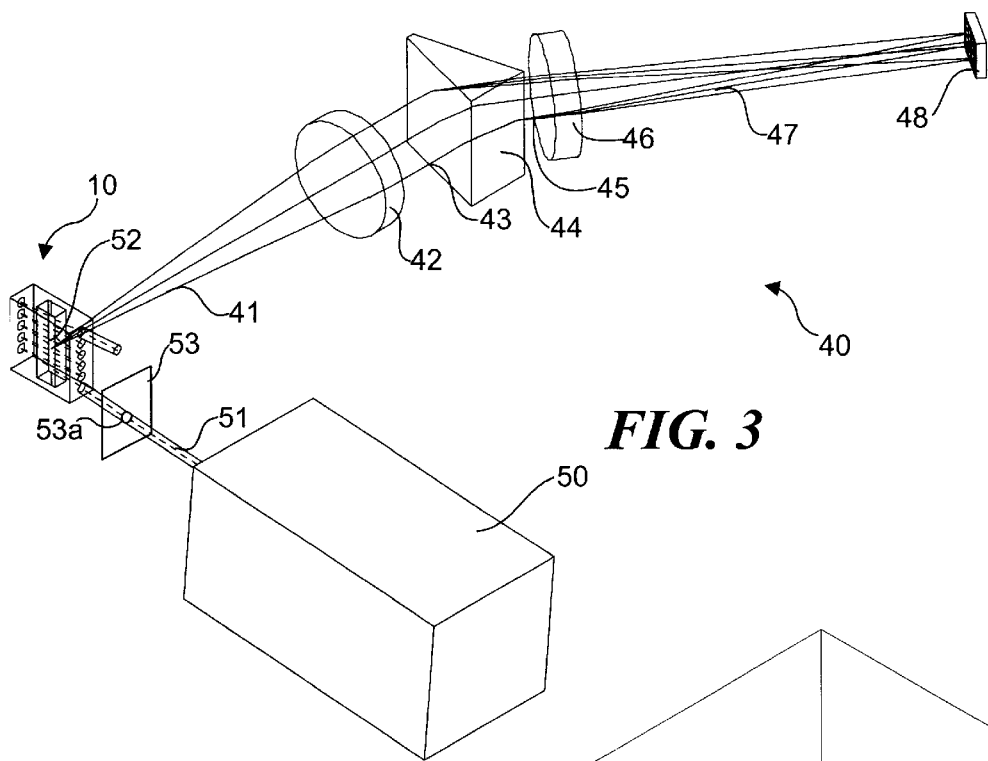
FIG. 3 is an isometric view of an exemplary imaging system that implements the illumination system of FIG. 1.

FIG. 3 shows an exemplary imaging system 40 that is substantially similar to imaging systems disclosed in copending commonly assigned U.S. Pat. No. 6,249,341, the specification and drawings of which have been specifically incorporated herein by reference. The present invention is employed for illumination in imaging system 40. In this imaging system, light 41 from an object passes through a collection lens 42, which collects the light, producing collected light 43. The collected light is focussed substantially at infinity, i.e., the rays of collected light 43 are generally parallel and enter a prism 44, which disperses the light, producing dispersed light 45. The dispersed light enters an imaging lens 46, which focusses light 47 on a time-delay-integration (TDI) detector 48.

Imaging system 40 includes illumination system 10, which was discussed above. A laser light source 50 directs a beam of coherent light 51 toward a reflection cavity 52 within illumination system 10, as shown in the Figure. Optionally, the illumination system may further include an aperture plate 53, which includes an aperture 53a having a diameter selected to reduce the size of the beam sufficiently so that the light intensity distribution across the cross section of the beam that has passed through the aperture is substantially constant. It should be noted that the present invention may be included in other imaging systems that are described and illustrated in the above referenced copending patent application.

Figure 4:
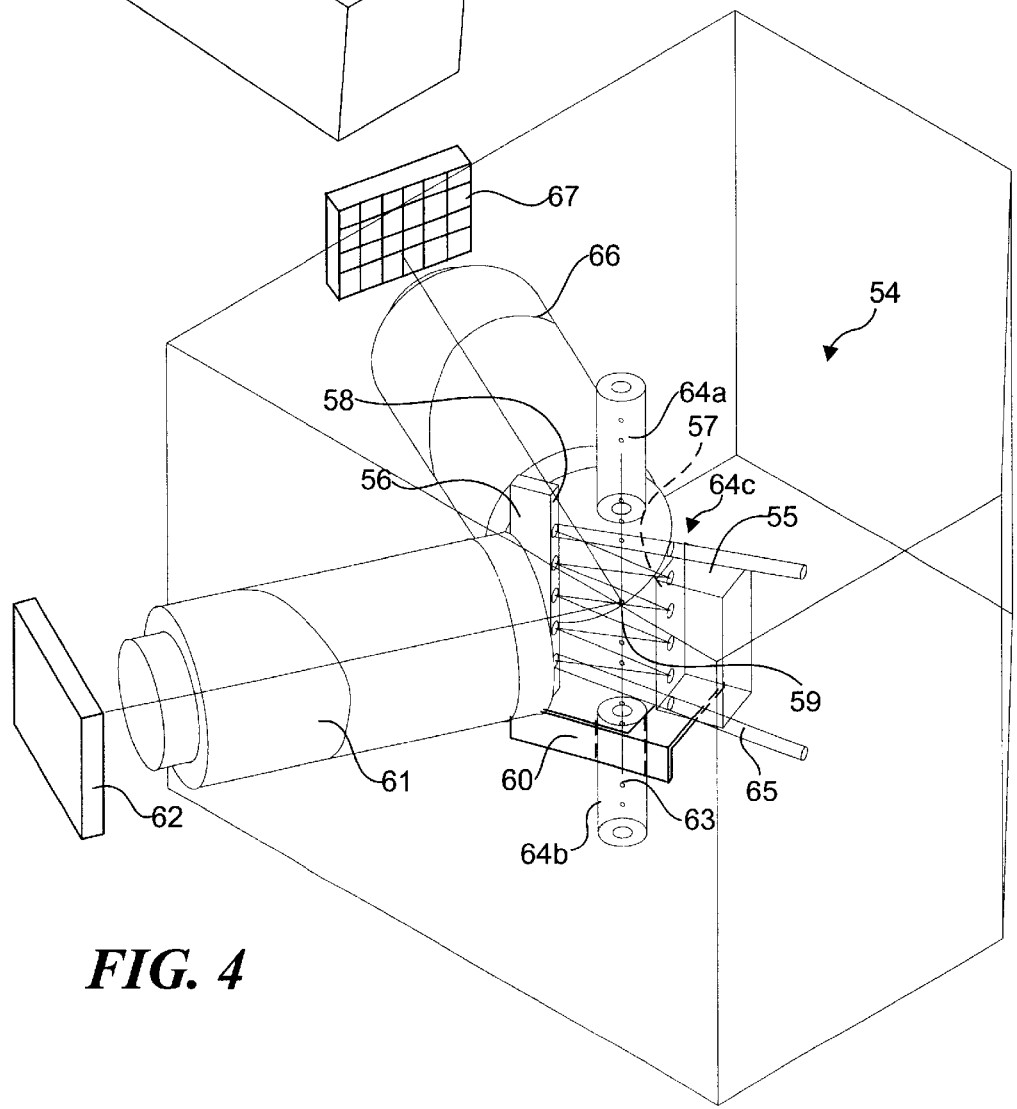
FIG. 4 is an isometric view of an embodiment of the present invention using mirrors immersed in a fluid.

The present invention can also be configured for implementation in a stereoscopic imaging flow cytometer. This configuration of the present invention is shown in FIG. 4 where a reflection cavity 59 is created by supporting two mirrors 55 and 56 on independent substrates within an immersion medium of an imaging flow cytometer. The ends of two capillary tubes 64a and 64b are brought within close proximity to each other. A stream of objects 63 is hydrodynamically focused with capillary tube 64a and caused to flow through a gap 64c between the tubes and into capillary tube 64b. Two water immersion objectives 61 and 66 are mounted on a frame (not shown) and are employed to image the gap between the capillary tubes onto two pixilated detectors 62 and 67. Mirrors 55 and 56, which are supported within the immersion cavity on a frame 60, create reflection cavity 59 around the stream of objects 63. Light from an illumination source (not shown) is directed along a path 65 under mirror 55, through stream of objects 63, and onto mirror 56. Upon striking the mirror, the light is redirected back through stream of objects 63, and caused to again traverse the stream of objects, generally in the manner described above, in regard to FIG. 1.

The foregoing Figures illustrate several of the various optical system configurations that include the present invention. Those skilled in the art will appreciate the present invention may be used to advantage in imaging as well as non-imaging flow cytometers. The following discussion numerically quantifies the advantage of using an embodiment of the present invention in a non-imaging PMT-based flow cytometer. The signal strengths are compared for three different illumination systems, two of which are in the prior art, and one of which is an embodiment of the present invention.

Figure 5:
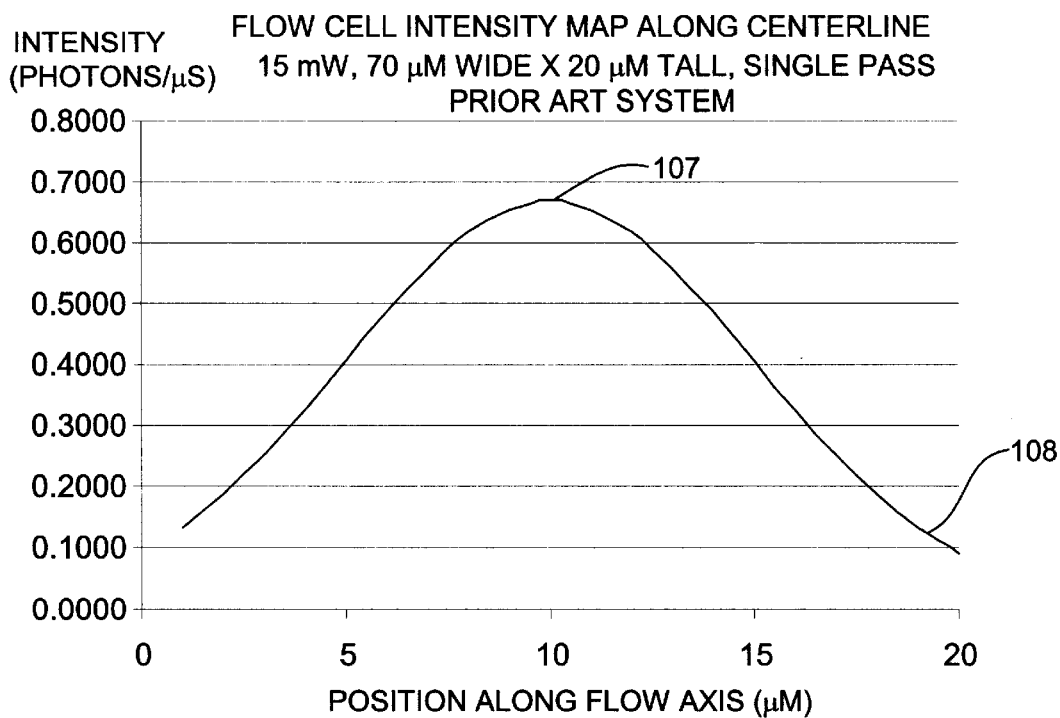
FIG. 5 is an XY plot showing an illumination intensity profile for a conventional (Prior Art) single pass illumination scheme with a short FOV.

The first prior art system to be discussed is incorporated in a widely-available, non-imaging commercial flow cytometer system. This system employs a 15 mW continuous wave laser that produces an elliptical beam spot 70 microns wide by 20 microns tall, a 6 m/s sample flow rate, and a PMT detector (not shown). An intensity profile along a flow path of the illumination system is illustrated in FIG. 5. The profile has a peak intensity 107 that is approximately 0.68 photons/microsecond through the area defined by the absorbance cross section of a fluorescein molecule. The intensity varies over the field of view of the collection system in accordance with a Gaussian distribution function, $1/e^{2x}$, wherein "x" is a ratio of the distance along the traversal path to the radius of the beam. Conventionally, the boundaries of a Gaussian beam are defined at a $1/e^2$ point 108, which is the position at which the intensity falls to approximately 13% of the peak intensity. For this illumination profile, each fluorescein molecule emits an average of 1.29 photons as it traverses the illuminated region. Those skilled in the art will appreciate that the emission of photons is quantized (no fractional photons are emitted) and that some molecules emit no photons, while others emit one or more photons when traversing the illuminated region. However, the resulting average number of emissions per molecule over all molecules is a fractional number.

Figure 6:
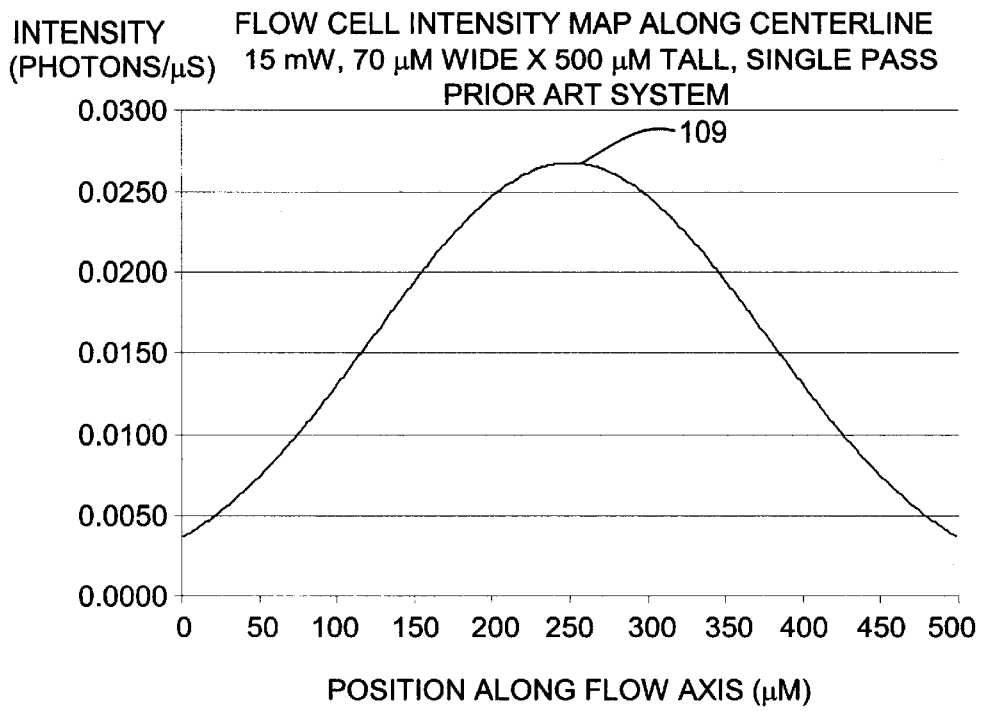
FIG. 6 is an XY plot showing an illumination intensity profile for a conventional (Prior Art) single pass illumination scheme with a tall FOV.

The second prior art example is the same as the first except that the dimension of the illuminating beam is 500 microns in the axis parallel to the direction of object flow. FIG. 6 illustrates an intensity profile for the enlarged illumination area produced by this second prior art system. A peak intensity 109 for this profile is approximately 0.027 photons/microsecond, which is 25 times lower than in the first example shown in FIG. 5. Despite the lower peak intensity, the average emission per fluorescein molecule remains 1.29 photons due to the increased illumination time allowed by the taller beam. Because there is no difference in the average emission per fluorescein dye molecule in the two prior art systems, there is no change in instrument performance, despite the 25-fold change in beam height. Changes in the beam height along the axis of the flow stream do not change the number of fluorescent photons emitted by the sample as it flows through the illuminated region, because the increased illumination time is offset by a corresponding reduced photon flux per unit area.

Figure 7:
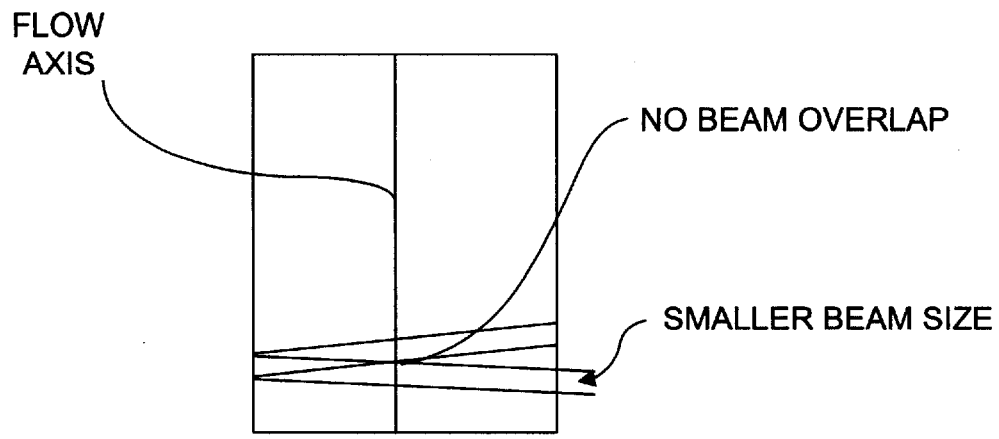
FIG. 7 is a schematic diagram illustrating a condition in which no beam overlap occurs at the center of the cavity when a smaller beam size is used in a preferred embodiment of the present invention.

FIG. 7 illustrates an embodiment of the present invention wherein the beam height is 100 microns in the axis parallel to flow, and the beam is reflected across the illuminated region five times. The beam incident angle is inclined relative to the reflecting surfaces so that there is no overlap of the beam in the center of the cavity. The resulting total illuminated height is therefore 500 microns, like that of the second prior art example discussed just above. In this embodiment of the present invention, the beam width is increased from the 70 micron dimension in the prior art, to 90 microns in order to reduce beam divergence. With the configuration used in this embodiment of the present invention, the average number of photons emitted per dye molecule is increased to 4.78 photons, more than a factor of three greater than is obtained using conventional illumination in the prior art. The increase in emitted photons is a result of two factors: (1) high illumination flux due to compact beam dimensions; and (2) an extended illumination height (and correspondingly longer illumination time), due to the multiple offset passes of the laser beam through the illumination region.

Figure 8:
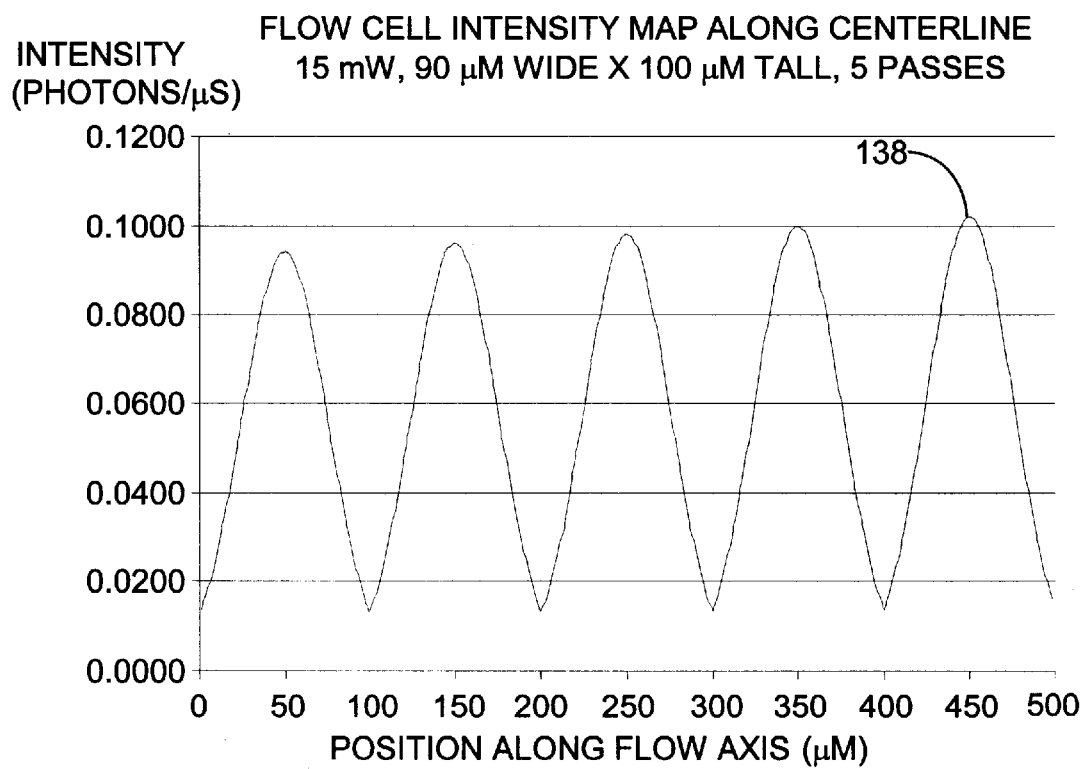
FIG. 8 is an XY plot showing an illumination intensity profile for the embodiment of the present invention illustrated in FIG. 7, but for the case in which a narrow light beam passes through a field of view five times.

The intensity profile along the stream axis, which provides the increased illumination flux of the above embodiment, is illustrated in FIG. 8. From FIG. 8, it is apparent that a five-pass embodiment produces a peak intensity 138 of more than 0.10 photons/microsecond through the area defined by the absorbance cross section of the fluorescein molecule, which is four times greater than that shown in FIG. 6 for the prior art illumination configuration with the same illumination height. The increase in intensity of the exciting beam and the increase in the number of passes in which the exciting beam encounters a molecule in the present invention produce more fluorescence from each molecule of the dye.

Figure 9:
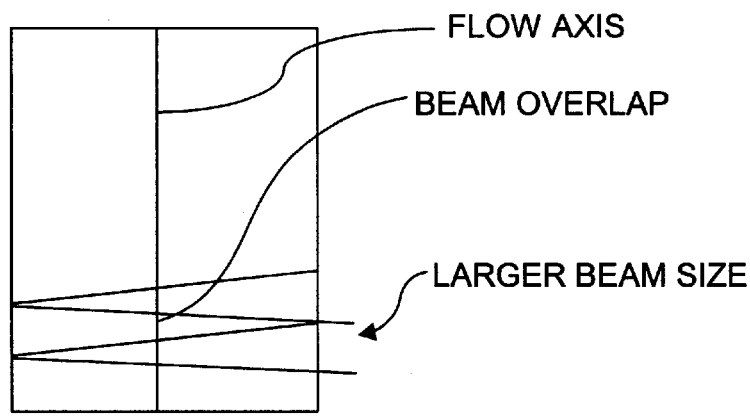
FIG. 9 is a schematic diagram illustrating a condition in which significant beam overlap occurs at the center of the cavity when a larger beam size is used in a preferred embodiment of the present invention.
Figure 10:
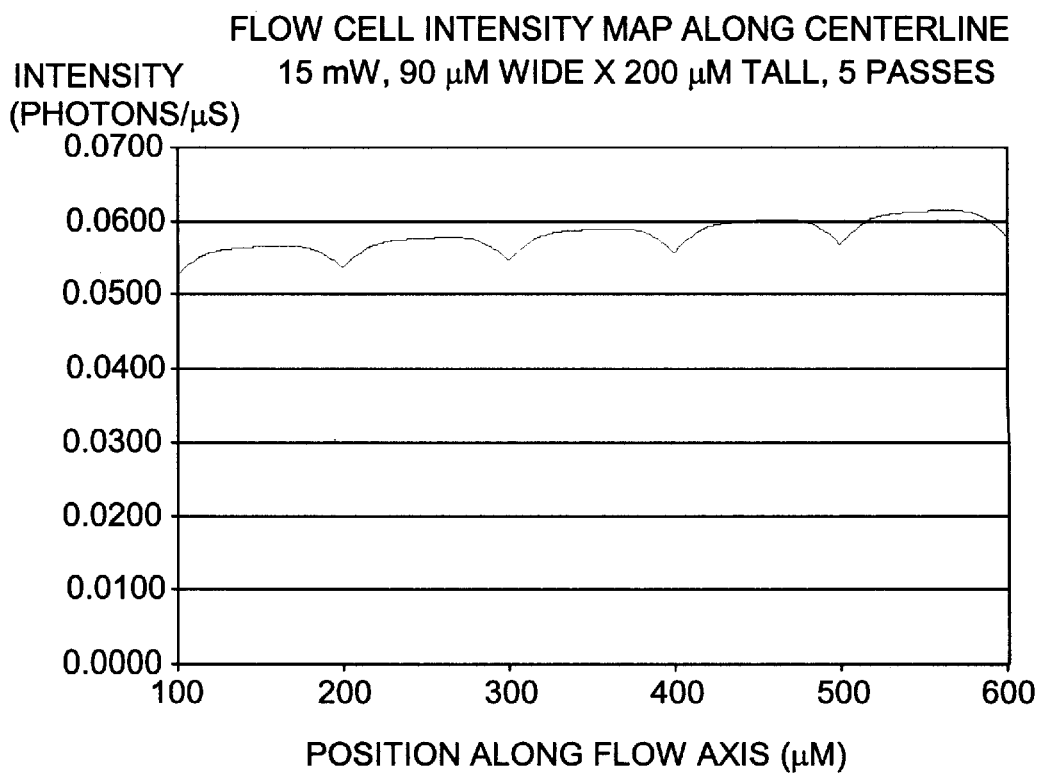
FIG. 10 is an XY plot showing an illumination intensity profile for the embodiment of the present invention illustrated in FIG. 9, but for the case in which a wide light beam passes through a field of view five times.

In addition to increasing illumination intensity, the present invention enables control of the illumination intensity profile in the cavity at the intersection of the stream and each of the plurality of beam passes. By appropriately choosing a waist size and the incident angles, an advantageous illumination profile may be achieved. For applications of the present invention in imaging flow cytometers, it may be advantageous to create a more uniform illumination intensity profile in the cavity, to decrease measurement variation. FIG. 9 shows a configuration similar to that of FIG. 7, except that the beam height is increased to produce a 50% overlap between beam segments in adjacent passes. FIG. 10 shows the resulting intensity profile, which is of much higher uniformity than is produced under no-overlap conditions. In addition to changing the beam size, the extent of beam overlap from pass to pass can be controlled by modifying the distance between the cavity's reflective surfaces and by changing the incident angle of the beam. Increasing the distance between the reflective surfaces and/or the incident angle allows the beam to propagate farther along the vertical axis between passes across the center of the cavity.

Figure 11:
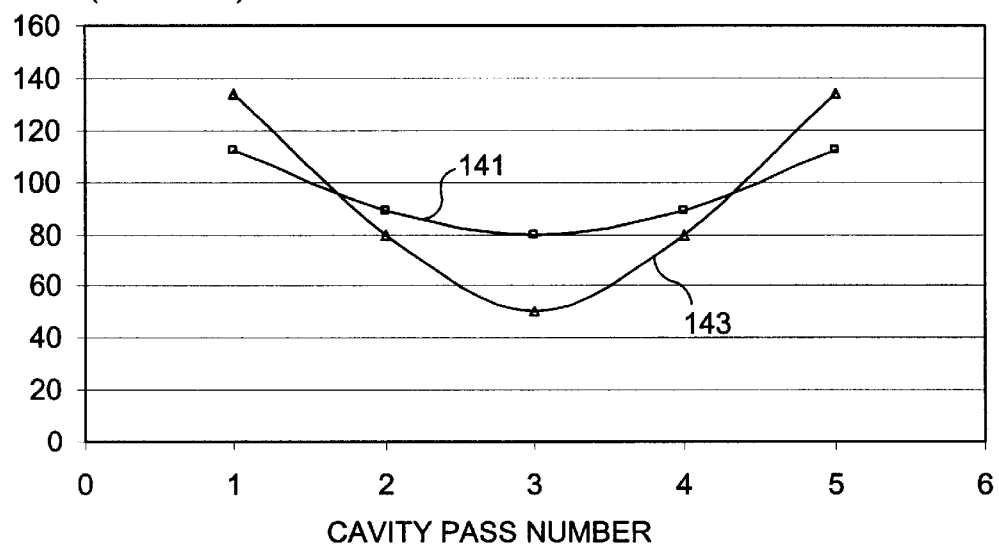
FIG. 11 is a plot of the beam size in the horizontal axes for two beams with different waist sizes in a five pass embodiment of the invention, illustrating how a larger waist size can produce a smaller average beam size, thereby increasing the overall intensity of light incident on the stream.
Figures 13A, 13B, 13C:
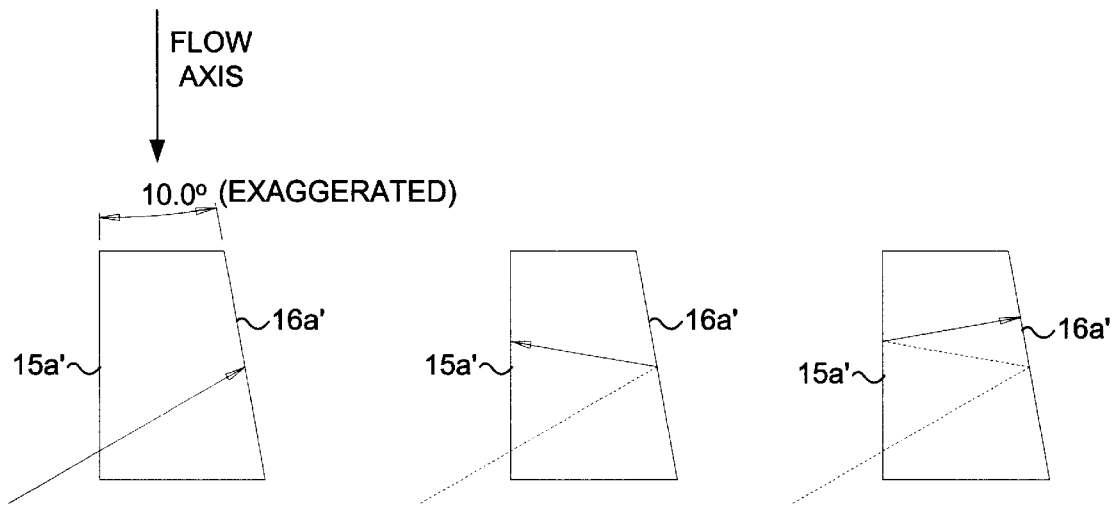
Figures 13D, 13E, 13F:
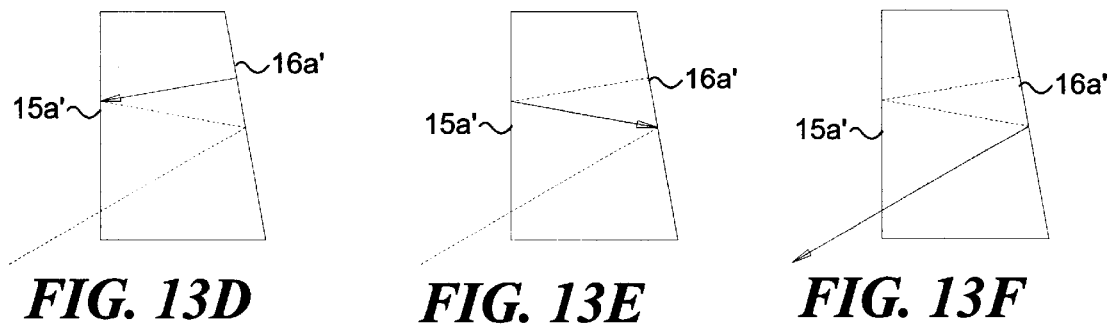

In addition to the factors that cause beam overlap noted above, beam overlap can occur as a result of a divergence of the beam as it traverses the cavity. Divergence due to diffraction causes the cross-sectional area of the beam to increase as the beam traverses the cavity. As the traversal distance increases, a concomitant increase in cross-sectional beam area, or beam spread occurs. This increase in beam spread decreases the intensity, or photon flux at any given portion in the cross section of the beam, which in turn, reduces the probability of fluorescence excitation of probe molecules. Therefore, the beam spread must be kept within acceptable limits. In accord with the embodiments of the present invention discussed above, the beam waist, i.e., the point of the smallest cross-sectional area of the beam, is preferably at a midpoint of the beam traversal through the cavity. The beam cross-sectional size increases in either direction away from the waist at a rate that is inversely proportional to the size of the waist. This phenomenon is illustrated in FIG. 11, which shows the spread of two beams over five passes across the center of a 5 mm wide cavity, one beam having a 50 micron waist (line 141 with triangles at data points) and the other an 80 micron waist (line 143 with squares at data points). Even though a 50 micron waist is substantially smaller in diameter than an 80 micron waist, the average beam diameter throughout the entire traversal of the 50 micron beam is larger. Those skilled in the art will appreciate that in view of the beam divergence, the waist size may be chosen appropriately to maximize intensity based on the number of cavity traversals and the acceptable beam size at points away from the waist, or in regard to the average beam size within the cavity. Those skilled in the art will also appreciate that the beam waist may be disposed appropriately within or outside the cavity to achieve a desired effect with the present invention.

Within the scope of the present invention, various parameters can be adjusted to increase the number of cavity traversals the beam makes while maintaining a beam size that is appropriate to increase fluorescence. For example, the cavity may be made narrower to decrease the path length that the beam must travel as it traverses the cavity. In this manner, the number of passes in the cavity can be increased while still maintaining a small cross-sectional beam size and thereby maintaining relatively high beam intensity.

FIG. 12 shows an embodiment of illumination system 10 in accord with the present invention in which a retro-reflector 139 is included to reflect the beam back into the cavity after it has exited the top of the cavity. In all other respects, the embodiment shown in this Figure is substantially identical to the first preferred embodiment shown in FIG. 1. However, in the embodiment of FIG. 12, retro-reflector 139 reflects the beam back along the path it followed before exiting the cavity, so that the beam reversing its previous path through the substrate. This embodiment effectively doubles the number of beam passes through the cavity achieved by the embodiment in FIG. 1. A 20-pass retro-reflected embodiment will provide nearly a 15-fold increase in the average photon exposure of an object over a conventional single-pass illumination.

FIGS. 13A–13F illustrate another embodiment of the present invention wherein the beam traverses the cavity and reverses direction, but unlike the embodiment of FIG. 12, it does so without the use of a retro-reflector. In this embodiment, an angle is introduced between two surfaces 15a' and 16a', which comprise the walls of the cavity. For illustration purposes, the angle between the reflecting surfaces is exaggerated and shown as equal to ten degrees. As will be observed in the Figure, the introduction of the angle between the two surfaces causes a gradual reduction in the incident angle of the beam relative to the surfaces, as the beam repeatedly traverses the cavity. Eventually, the incident angle becomes 90 degrees, or reverses sign, and the beam is reflected back upon itself (or down the walls of the cavity) and re-traverses the cavity in the opposite direction.

As illustrated earlier in FIG. 11, the cross-sectional beam size converges to a minimum at the waist position then diverges. The intensity of the beam at any point is inversely proportional to the square of the beam diameter. In order to maintain a high beam intensity, it is therefore advantageous to maintain a small beam diameter as the beam traverses the cavity. To achieve this goal, the embodiment of the present invention shown in FIGS. 14A and 14B incorporates optical power in the reflecting surfaces of the cavity. Each wall of the cavity is a cylindrical mirror 151 and 153 with curvature in the horizontal plane selected to focus the light beam that is reflected therefrom within the cavity. The center of each wall's radius of curvature, R, is the flow stream, so with each reflection of the light beam, the diverging beam is refocused by the mirrors on the objects within the flow stream. As a result, a small beam diameter is maintained in the vicinity of the flow stream, and the beam spread in the axis perpendicular to flow is minimized so that more light is focused on the objects in the stream than could otherwise be obtained. The embodiment shown in FIGS. 14A and 14B also incorporates the method of beam reversal illustrated in FIGS.

13A–F. The size of a 488 nm laser beam waist in the vertical and horizontal axes for this embodiment is plotted in FIG. 15. The beam size in the axis perpendicular to flow is maintained at 40 microns in the vicinity of the flow stream. As the beam propagates up the cavity, the beam diameter alternately converges on the flow stream and then diverges toward the reflecting surface where, upon reflection, the beam re-converges near the flow stream. In this embodiment of the present invention, the cylindrical surface contains no optical power in the axis of flow. Therefore, the beam diameter upon the first intersection with the stream is 199 microns. The beam continues to converge up to the $14^{th}$ pass where the beam waist, or minimum beam diameter, of 91 microns is reached. The use of the tilted surface wall or the use of a retro-reflector where the beam exits enables the beam to traverse back down the cavity, providing a total of 28 passes of the beam through the flow stream. A flow cytometer employing this embodiment, with a 28-pass cavity, produces an average photon emission per dye molecule of 44.32 photons. This result represents a 35-fold increase in signal strength compared to the conventional method of illumination, where only a 1.29 photon per molecule average emission is achieved.

As a further embodiment of the present invention, optical power can be provided in both the vertical and horizontal axes of the cavity walls. FIG. 16 illustrates an alternative embodiment of the present invention where the reflection cavity surfaces 161 and 163 are toroids with a radius of 50 mm about an axis perpendicular to the page and a radius of approximately 1 mm about the axis along the flow stream. The centers of curvature for the 50 mm surfaces are separated by approximately 98 mm, so that the vertex of each mirror is separated by 2 mm and centered on the flow stream axis. The illumination beam enters the reflective cavity perpendicular to the flow stream axis at a point approximately 1 mm below the axis defined by a line running between the centers of curvature for the two 50 mm surfaces. Along the axis of beam propagation, the beam waist is located within the reflective cavity and the beam makes a first flow stream intersection. The beam traverses the cavity and is reflected upward at an angle of approximately 2.3 degrees from horizontal, causing the beam to re-cross the cavity and strike the other wall of the cavity. The beam reflects from this cavity wall at an angle of about 4.4 degrees with respect to horizontal and continues to re-cross the cavity and strike the opposite surface in this manner such that the reflected angle with the horizontal increases upon each reflection of the beam by one of the surfaces. After the sixth reflection, the beam traverses the cavity and crosses the axis defined by a line 165 running between the centers of curvature of the two 50 mm radii surfaces 161 and 163. At this point, the normals to these surfaces point downward. Therefore, the reflected angle of the beam with respect to the horizontal decreases. At the first reflection after the beam crosses the axis defined by the centers of curvature of the surfaces, the reflection angle of the beam with respect to the horizontal is approximately 8.1 degrees. At the second reflection after crossing the axis, the reflection angle is reduced to approximately 7.4 degrees. At the eleventh reflection, the beam makes an angle of approximately zero degrees to the horizontal, and after striking the other wall, the propagation direction of the beam with respect to the flow axis is reversed. The beam then propagates down the cavity, reflecting from the surfaces and eventually exits the cavity at its point of entry after making twenty two passes through the flow stream.

FIG. 17 illustrates the beam waist size during the propagation of a 488 nm laser beam through the embodiment of the invention illustrated in FIG. 16, where the reflecting surfaces have optical power in both axes. The beam intersects the flow stream on the first pass with a 50 micron waist in each axis. After the beam passes through the stream it begins to diverge and strikes the far wall of the cavity. Upon reflection, the beam re-converges in the vertical plane such that the waist is approximately 50 microns when it crosses the flow stream. As described in the previous embodiment the beam always re-converges at the flow stream with a waist size of 50 microns in the vertical plane after striking the cavity wall. However, in the axis parallel to flow the beam continues to diverge after reflecting off the cavity wall. The optical power in that axis is insufficient to cause the beam to re-converge. Therefore, when the beam intersects the flow axis on the second pass, it is approximately 55 microns in the axis parallel to flow. The optical power in the axis parallel to flow reduces the divergence from what it would be if the surface contained no optical power in the that axis, but the divergence continues to increase as the beam enters the far field propagation regime. Ultimately, after reflecting from the left hand and right hand surfaces of the cavity eleven times, the beam begins to re-converge in the axis parallel to flow. At this point the beam waist is approximately 176 microns. From this point on the beam begins to converge back toward a 50 micron waist, but exits the cavity before reaching a dimension of 50 microns in the axis parallel to flow.

Those skilled in the art will appreciate that in all the cases described thus far, the F-number of each of the optical systems described is in excess of 40 and therefore, from an aberration perspective, the optical performance is very well behaved, and the spot sizes of the beam in each axis are dictated by diffraction theory. Therefore, constant radius surfaces may employed. However, those skilled in the art will also appreciate that for lower F-numbers, or smaller spot sizes, aspheric or non-constant radii surfaces may be employed to control wave front aberrations.

Active Cavity Beam Detection

The present invention can be equipped with an active beam detection and alignment system, to maintain optical alignment of the input laser beam to the multipass cavity. Beam misalignment in a multipass cavity has four degrees of freedom, position in the horizontal (X) and vertical (Y) directions and angle in the vertical and horizontal axes, termed tip and tilt respectively. That definition of tip and tilt should be applied to the following disclosure and the claims that follow.

FIG. 18 illustrates a beam detection system 212 that can be used to quantify both the positional and angular error of a beam of light exiting the cavity of a flow cell. Further, the error for all four degrees of freedom can be quantified independently. The embodiment shown in FIG. 18 depicts the arrangement for a beam of light leaving the cavity through a cavity exit aperture 170. However the same principles can be applied for a portion of the beam of light split off from the main beam before entering the cavity, as is shown in FIG. 20.

After the beam of light leaves the cavity through exit aperture 170, it passes through a lens element 172, which is followed by an amplitude beam splitter 174, which splits the beam into two optical paths, according to the beam splitter coating transmission to reflection ratio T/R. In a preferred embodiment the T/R ratio is 50/50 to provide approximately 50% of the incident light into each optical path. The reflected beam is directed onto a position sensitive detector 176, such as a quadrant detector or quad cell. The transmitted beam passes through lens element 178, and is then directed onto a second quad cell 180.

Lens element 172 is positioned such that its front focal plane is located at the cavity exit aperture 170 The first quad cell (Angle Quad Cell), position sensitive detector 176, is placed behind a rear focal plane of lens 172. Note that position sensitive detector 176, is shifted off of an optical axis 190 by beam splitter 174. A beam 182 exiting cavity exit aperture 170 with an angular error 184 will be imaged by lens 172 laterally displaced from the center of position sensitive detector 176. Because exit aperture 170 is at the front focal plane of lens 172, all beams of the same angle will be focussed at the same location on position sensitive detector 176, independent of their position in cavity exit aperture 170. As the beam angular error changes horizontally and vertically, the focused beam position on the quad cell will change in both the X and Y direction. Thus the Angle Quad Cell determines the tip and tilt error in the beam.

A beam 186 leaving cavity exit aperture 170 with no angular error, but with a lateral position error 188, will be imaged by lens 172 at the center of the position sensitive detector 176. Because cavity exit aperture 170 is at the front focal plane of lens 172, all beams with no angular error, i.e. any beams that are parallel to optical axis 190, will be focussed to the center of position sensitive detector 176, independent of their position relative to cavity exit aperture 170. Therefore, the Angle Quad Cell (position sensitive detector 176) will detect only angular errors of the beam, and will not be affected by position errors.

Lens element 178 is positioned to receive the light transmitted through beam splitter 174. The Position Quad Cell (second quad cell 180) is located at the rear focal plane of lens 178. By virtue of these lens positions, an image of cavity exit aperture 170 is formed on the Position Quad Cell (second quad cell 180) with a lateral magnification determined by the ratio of focal lengths of lens element 178 to lens element 172. The magnification of the system can be made greater than 1 to increase the sensitivity of position error detection at the Position Quad Cell (second quad cell 180). Therefore, the Position Quad Cell can be used to measure the positional error of the beam at cavity exit aperture 170. Note that the positional error includes both the lateral error as described above, as well as any error along the Y axis of cavity exit aperture 170 (an up or down deviation from the center axis of cavity exit aperture 170). With reference to the claims that follow, it should be understood that the term "positional error" encompasses non-angular errors, including errors about both the X axis of cavity exit aperture 170 (a lateral deviation from the center axis of cavity exit aperture 170) and the Y axis of cavity exit aperture 170 (an up or down deviation from the center axis of cavity exit aperture 170).

Those skilled in the art can appreciate that because cavity exit aperture 170 and Position Quad Cell (second quad cell 180) are at conjugate image planes, the position of the beam can be measured at this point independent of the angle of the beam at cavity exit aperture 170. For clarity, FIG. 18 illustrates a magnification of unity for exit aperture 170 imaged onto second quad cell 180 (the Position Quad Cell). In practice the magnification will be greater than unity. In one embodiment a magnification of 5× is employed by using focal lengths of 50 mm and 250 mm for lenses 172 and 178, respectively.

Active Cavity Beam Alignment

Active cavity beam detection system 212 of FIG. 18 allows for the measurement of beam misalignment to the multipass cavity in an independent fashion for each degree of freedom X, Y, tip and tilt. To facilitate active alignment of an input laser beam to the multipass cavity it is desirable to have independent control over these parameters in the input optical system.

FIGS. 19A, 19B, and 19C each show plan views of an optical system 210 that provides for independent control of the beam position and angle at the input aperture of the multipass cavity. In FIG. 19A, system 210 is shown in an aligned condition. The collimated (e.g., light rays substantially focussed to infinity) input laser beam 192 is redirected by a first reflective element 194, placed at the front focal plane of a lens 196, and is focused at the rear focal plane of a lens 196, where a second reflective element 198 is disposed. Reflective element 198 is also located at the front focal plane of a lens 200. After redirection by reflective element 198, the laser beam is recollimated by lens 200, before entering a multipass cavity aperture 202, which is located at the rear focal plane of lens 200. In this arrangement, multipass cavity aperture 202 is effectively collimated by lens 200 at reflective element 198. Multipass cavity aperture 202 is also imaged by lens 196 onto reflective element 194.

As in the beam detection system, by virtue of this optical arrangement, independent control of the 4 degrees of freedom is obtained. In FIG. 19B, first reflecting element 194, also referred to as the Angle Adjustment Mirror, is adjusted in angle to produce a positional change of the beam at second reflecting element 198. This positional change of the beam at the front focal plane of lens 200 results in an angular change of an input beam 204 at cavity input aperture 202.

In FIG. 19C, the Angle Adjustment Mirror (first reflecting element 194), is shown in the aligned position with the laser beam centered on second reflective element 198, which is also referred to as the Position Adjusting Mirror. The Position Adjustment Mirror (second reflective element 198), is adjusted in angle, and because it is at the front focal plane of lens 200, it produces only a positional change in beam 206 at cavity input aperture 202. Therefore, independent control of all four degrees of freedom X, Y, tip and tilt are provided by this optical system.

FIG. 20 is a plan view of an integrated beam detection and alignment system in which active cavity beam detection system 212 of FIG. 18 has been added to the beam alignment optical system 210 of FIGS. 19A–C, by employing a beam splitter. In FIG. 20, beam splitter 208 is disposed in the optical path before the entrance to the multipass cavity, and samples the laser light as it exits the cavity. The beam splitter ratio T/R is chosen so as to maximize the transmission of the input laser beam, while providing sufficient reflected light to ensure adequate signal to noise for the beam detection system. By sampling the laser beam after it leaves the multipass cavity, errors in beam alignment due to movement of the cavity itself, such as might be caused by system vibrations, can be corrected. However, it is anticipated that alternate embodiments could sample the beam as it enters the multipass cavity, e.g. by changing the angle of beam splitter 208 by 90 degrees in the plane of FIG. 20.

FIG. 21 is a functional block diagram showing the major components of a closed-loop active cavity alignment system. In FIG. 21, light from beam alignment optical system 210 is sampled and imaged onto the paired quad cell detectors of active cavity beam detection system 212. The Angle Quad Cell (position sensitive detector 176) measures the angle of the beam as it exits multipass cavity aperture 202. The Position Quad Cell (second quad cell 180) measures the position of the beam as it exits multipass cavity aperture 202. A Beam Alignment Processor 214 analyzes the output from Beam Detection System 212, and measures the error in the beam position or angle as it leaves multipass cavity aperture 202. A System Controller 216 retrieves the measurements from Beam Alignment Processor 214 and corrects angular and positional errors in laser input beam 192 by employing Motorized Mirror Mounts 220 and a Motor Driver 218 to effect the required adjustments to beam alignment optical system 210. Motorized mirror mounts incorporate motorized actuators that adjust the mirror angle in two axes, tip and tilt. It should be noted that one or more of processor 214 and controller 216 can be either a computing device (such as a personal computer) or a logical circuit (such as an application specific integrated circuit (ASIC)).

FIG. 22 illustrates a flow chart showing the sequence of logical steps in a method for actively controlling beam alignment optical system 210, to ensure the precise alignment of the beam to multipass cavity aperture 202. When the method begins, Beam Alignment Controller 214 reads the output of Angle Quad Cell (position sensitive detector 176) in a block 222, and converts that value into a measurement of the angular error of beam, relative to the optical axis of the multipass cavity aperture 202, in a block 224. If it is determined that the angular error exceeds a predetermined threshold in a decision block 226, Beam Alignment Controller 214 calculates a corrected position for the Angle Adjustment Mirror (first reflecting element 194) that eliminates the error in the angle of the beam as it leaves the cavity in a block 228.

Next, System Controller 216 queries the measurements and moves the Angle Adjustment Mirror (first reflecting element 194) to the new position to eliminate the detected error, in a block 230. Then Beam Alignment Processor 214 reads the output of Position Quad Cell (position sensitive detector 176) in a block 232 converts the value into a measurement of the positional error of beam relative to the optical axis of the cavity, in a block 234. Referring once again to decision block 226, if it is determined that the angular error does not exceed a predefined limit, then the logic moves from block 226 directly to block 232, and the logic reads the output of Position Quad Cell as described above.

Referring now to a decision block 236, the positional error is compared to a predetermined threshold. If the error is greater than the predetermined threshold, Beam Alignment Processor 214 calculates a corrected position for Position Adjustment Mirror (second reflective element 198) that eliminates the error in the position of the beam as it leaves the cavity, in a block 238. Once the corrected position is determined, System Controller 216 moves the Position Adjustment Mirror (second reflective element 198) to the new position to eliminate the detected error, in a block 240. The method is then complete. If in decision block 236 it is determined that the error determined in block 234 does not exceed the predetermined threshold, the method is similarly completed.

Alternate Embodiments

An alternate embodiment of the beam detection system is illustrated in FIG. 23. In this embodiment, two elongate mirrors 242 and 244 are used to reflect the beam back and forth to increase the path length of the beam, before it strikes the Angle Quad Cell (position sensitive detector 176). By increasing the path length, the angular error in the beam is magnified at the quad cell. This embodiment does not decouple the angular and positional errors on each quad cell. However, there is a deterministic trigonometric relationship between the errors seen on each quad cell that can be computed to factor out the source of each error. If imaging lens 178 is used to image cavity exit aperture 170 at the Position Quad Cell (second quad cell 180) as previously described, then the Position Quad Cell (second quad cell 180) measures the position error directly, and this can be subtracted from the Angle Quad Cell measurement to determine the angular error.

In regard to beam alignment optical system 210 and all other optical systems described herein, it will be understood that the lenses and other optical elements illustrated are shown only in a relatively simple form. Thus, while focusing lenses 196 and 200 are illustrated as compound lenses with two elements, such as cemented achromatic doublets, lens elements of different designs, either simpler or more complex, could be used in constructing the imaging system to provide the desired optical performance, as will be understood by those of ordinary skill in the art. Lens elements may be conventional ground and polished or molded glass or plastic lenses with spherical or aspheric surfaces, reflective optics with power or diffractive optical elements. Compound optical systems may include both transmissive and reflective optics of any of the above type. In addition, beam splitter optical components such as beam splitter 208 may be of the plate type as illustrated, with the beam splitter optical coating deposited on one surface; or the cube type, with the coating surface bonded between two prism elements, or the pellicle type. Reflective elements 194 and 198 may be plane mirrors as shown with metallic, dielectric, or hybrid (metallic and dielectric) type optical coatings deposited on the mirror surface. Prism elements may also be used for reflecting the beam, employing total internal reflection from uncoated surfaces, or with reflective optical coatings of the metallic, dielectric, or hybrid type deposited on the reflective face of the prism.

Other alternate embodiments include the use of spatial detectors other than the quad cell type, such as pixelated detectors, including Charge Coupled Devices (CCDs) and complementary metal-oxide semiconductors (CMOS) detectors to be used in the place of quad cells in the beam detection optical system.

Although the present invention has been described in connection with the preferred form of practicing it and modifications thereto, those of ordinary skill in the art will understand that many other modifications can be made to the present invention within the scope of the claims that follow. Accordingly, it is not intended that the scope of the invention in any way be limited by the above description, but instead be determined entirely by reference to the claims that follow.

The invention in which an exclusive right is claimed is defined by the following:

1. A beam detection system for use with an illumination system, to enable detection of beam misalignment in four degrees of freedom, comprising:

(a) a beam splitter disposed in an illumination system light path, said illumination system light path originating in said illumination system, said beam splitter separating an illumination system light beam traveling along the illumination system light path into a first beam that is directed along a first light path and a second beam that is directed along a second light path;

(b) a first position sensitive detector disposed in said first light path to receive said first beam, said first position sensitive detector determining an angular error associated with said illumination system light beam; and (c) a second position sensitive detector disposed in said second light path to receive said second beam; said second position sensitive detector determining at positional error associated with said illumination system light beam.

2. The beam detection system of claim 1, further comprising a first optical element disposed such that a front focal plane of said first optical element is disposed facing an aperture of said illumination system, and a rear focal plane of said first optical element is disposed facing said beam splitter.

3. The beam detection system of claim 1, further comprising a second optical element disposed such that a front focal plane of said second optical element is disposed facing an aperture of said illumination system, and a rear focal plane of said second optical element is disposed facing said second position sensitive detector.

4. The beam detection system of claim 1, further comprising a first and second optical element, disposed such that light reaching said first position sensitive detector from said illumination system light path passes through said first optical element but not said second optical element, and light reaching said second position sensitive detector from said illumination system light path passes through both said first optical element and said second optical element.

5. The beam detection system of claim 4, wherein said beam splitter is disposed between said first and second optical elements.

6. The beam detection system of claim 1, wherein said beam splitter directs said first beam by reflection and directs said second beam by transmission.

7. The beam detection system of claim 6, wherein a transmission/reflection ratio of said beam splitter is substantially 50/50.

8. A beam detection system for use with an illumination system, to enable detection of beam misalignment in four degrees of freedom, comprising:
   (a) a first optical element disposed in an illumination system light path, said illumination system light path originating in said illumination system, such that a front focal plane of said first optical element is disposed facing an aperture of said illumination system;
   (b) a beam splitter disposed in said illumination system light path, said beam splitter receiving light from said illumination system that passes through said first optical element, said beam splitter separating an illumination system light beam traveling along the illumination system light path into a first beam that is directed along a first light path and a second beam that is directed along a second light path;
   (c) a first position sensitive detector disposed in said first light path to receive said first beam, said first position sensitive detector determining an angular error associated with said illumination system light beam;
   (d) a second optical element disposed in said second light path, such that a front focal plane of said second optical element is disposed facing said aperture; and
   (e) a second position sensitive detector disposed in said second light path to receive said second beam, such that a rear focal plane of said second optical element is disposed facing said second position detector, said second position sensitive detector determining a positional error associated with said illumination system light beam.

9. The beam detection system of claim 8, wherein said beam splitter is disposed between said first and second optical elements.

10. The beam detection system of claim 8, wherein said beam splitter directs said first beam by reflection and directs said second beam by transmission.

11. The beam detection system of claim 10, wherein a transmission/reflection ratio of said beam splitter is substantially 50/50.

12. The beam detection system of claim 8, wherein said illumination system light path and said second light path share a common axis.

13. The beam detection system of claim 8, wherein a focal length of said first optical element is smaller than a focal length of said second optical element.

14. A beam detection and alignment system for use with an illumination system, to enable detection and correction of beam misalignment at an aperture of said illumination system, comprising:
   (a) a first independently adjustable reflective element disposed in an illumination system light path, said first independently adjustable reflective element selectively redirecting said illumination system light path, thereby adjusting a beam angle at said aperture;
   (b) a second independently adjustable reflective element disposed in said illumination system light path, said second independently adjustable reflective element selectively redirecting said illumination system light path, thereby adjusting a beam position at said aperture;
   (c) a first beam splitter disposed in said illumination system light path, said beam splitter separating an illumination system light beam traveling along the illumination system light path into a first beam that is directed along a first light path and a second beam that is directed along a second light path, said second light path being directed at said aperture;
   (d) a second beam splitter disposed in said first light path, said second beam splitter separating an illumination system light beam traveling along said first light path into a first detection beam that is directed along a first detection light path and a second detection beam that is directed along a second detection light path;
   (e) a first position sensitive detector disposed in said first detection light path to receive said first detection beam, said first position sensitive detector determining an angular error associated with said illumination system light beam; and
   (f) a second position sensitive detector disposed in said second detection light path to receive said second detection beam; said second position sensitive detector determining at positional error associated with said illumination system light beam.

15. The beam detection and alignment system of claim 14, further comprising:
   (a) a first alignment optical element disposed in said illumination system light path, between said first independently adjustable reflective element and said second independently adjustable reflective element, such that said aperture is imaged by said first optical element onto said first independently adjustable reflective element; and
   (b) a second alignment optical element disposed in said illumination system light path, between said second independently adjustable reflective element and said aperture, such that said aperture is substantially collimated by said second optical element at said second independently adjustable reflective element.

16. The beam detection and alignment system of claim 15, further comprising:
   (a) a first detection optical element disposed in said first light path, such that a focal plane of said first detection optical element is disposed facing said aperture; and
   (b) a second detection optical element disposed in said second detection light path, such that a focal plane of said second optical element is disposed facing said aperture, and said second beam splitter is disposed between said first and second detection optical elements.

17. The beam detection and alignment system of claim 16, wherein a focal length of said first detection optical element is smaller than a focal length of said second detection optical element.

18. The beam detection and alignment system of claim 14, wherein each beam splitter directs a first beam by reflection and a second beam by transmission.

19. The beam detection and alignment system of claim 18, wherein the transmission/reflection ratio of said first beam splitter is selected to sample a portion of the energy in the illumination system light path so as to provide a sufficient signal-to-noise ratio for accurate detection of the light traveling along the illumination system light path, and the transmission/reflection ratio of said second beam splitter is selected to provide substantially the same signal level at each position sensitive detector.

20. The beam detection and alignment system of claim 14, wherein said first light path and said second detection light path share a common axis.

21. The beam detection and alignment system of claim 14, wherein said first beam splitter is oriented to split an illumination system light beam traveling along the illumination system light path into said first beam and said second beam after the illumination system light beam passes through said aperture a first time, is internally reflected, and passes through said aperture a second time.

22. The beam detection and alignment system of claim 14, further comprising:
   (a) a beam alignment processor electrically coupled to each of said first and second position sensitive detectors, said beam alignment processor determining angular and positional correction factors based on signals received from said first and second position sensitive detectors; and
   (b) a prime mover drivingly coupled to each independently adjustable reflective element, such that each independently adjustable reflective element is repositionable independently of the other, said prime mover being electrically coupled to, and controlled by, said beam alignment processor.

23. The beam detection and alignment system of claim 14, wherein each independently adjustable reflective element comprises a mechanical actuator operable to adjust a position of the independently adjustable reflective element, further comprising a beam alignment processor electrically coupled to each of said first and second position sensitive detectors, said beam alignment processor determining angular and positional correction factors based on signals received from said first and second position sensitive detectors and being electrically coupled to each mechanical actuator, thereby enabling said beam alignment processor to control and adjust the position of each independently adjustable reflective element, based on signals generated by said first and second position sensitive detectors.

24. The beam detection and alignment system of claim 23, wherein said mechanical actuators are operable to adjust a tip and a tilt of each independently adjustable reflective element.

25. A beam detection and alignment system for use with an illumination system, to enable detection and correction of beam misalignment at an aperture of said detection illumination system, comprising:
   (a) a first independently adjustable reflective element disposed in an illumination system light path, said first independently adjustable reflective element selectively modifying said illumination system light path by adjusting a beam angle at said aperture;
   (b) a second independently adjustable reflective element disposed in said illumination system light path, said second independently adjustable reflective element selectively modifying said illumination system light path by adjusting a beam position at said aperture;
   (c) a first alignment optical element disposed in said illumination system light path, between said first independently adjustable reflective element and said second independently adjustable reflective element, such that said aperture is imaged by said first optical element onto said first independently adjustable reflective element;
   (d) a second alignment optical element disposed in said illumination system light path, between said second independently adjustable reflective element and said aperture, such that said aperture is substantially collimated by said second optical element at said second independently adjustable reflective element;
   (e) a first beam splitter disposed in said illumination system light path, said first beam splitter separating said illumination system light beam into a first beam that is directed along a first light path and a second beam that is directed along a second light path, said second light path being directed at said aperture;
   (f) a second beam splitter disposed in said first light path, said second beam splitter separating said illumination system light beam into a first detection beam that is directed along a first detection light path and a second detection beam that is directed along a second detection light path;
   (g) a first detection optical element disposed in said first light path;
   (h) a second detection optical element disposed in said second detection light path, such that said second beam splitter is disposed between said first and second detection optical elements;
   (i) a first position sensitive detector disposed in said first detection light path to receive said first detection beam, said first position sensitive detector determining an angular error associated with said illumination system light beam; and
   (j) a second position sensitive detector disposed in said second detection light path to receive said second detection beam, said second position sensitive detector determining a positional error associated with said illumination system light beam.

26. The beam detection and alignment system of claim 25, wherein each independently adjustable reflective element comprises a mechanical actuator operable to adjust a position of the independently adjustable reflective element, further comprising a beam alignment processor electrically coupled to each of said first and second position sensitive detectors, said beam alignment processor determining angular and positional correction factors based on signals received from said first and second position sensitive detectors and being electrically coupled to each mechanical actuator to enable said beam alignment processor to control and adjust the position of each independently adjustable reflective element based on signals generated by said first and second position sensitive detectors.

27. A beam detection and alignment system for use with an illumination system, to enable detection and correction of beam misalignment at an aperture of said illumination system, comprising:

(a) a first independently adjustable reflective element disposed in an illumination system light path, comprising a mechanical actuator operable to adjust a position of said first independently adjustable reflective element, thereby selectively modifying said illumination system light path, to adjust a beam angle at said aperture;

(b) a second independently adjustable reflective element disposed in said illumination system light path, comprising a mechanical actuator operable to adjust a position of said second independently adjustable reflective element to selectively modify said illumination system light path, to adjust a beam position at said aperture;

(c) a first beam splitter disposed in said an illumination system light path, said beam splitter separating an illumination system light beam traveling along the illumination system light path into a first beam that is directed along a first light path and a second beam that is directed along a second light path, said second light path being directed at said aperture;

(d) a second beam splitter disposed in said first light path, said second beam splitter separating an illumination system light beam traveling along said first light path into a first detection beam that is directed along a first detection light path and a second detection beam that is directed along a second detection light path;

(e) a first position sensitive detector disposed in said first detection light path to receive said first detection beam, said first position sensitive detector producing a signal indicative of an angular error associated with said illumination system light beam;

(f) a second position sensitive detector disposed in said second detection light path to receive said second detection beam; said second position sensitive detector producing a signal indicative of a positional error associated with said illumination system light beam; and (g) a beam alignment processor electrically coupled to each of said first and second position sensitive detectors, and to each mechanical actuator, said beam alignment processor determining angular and positional correction factors based on the signals received from said first and second position sensitive detectors, and adjusting a position of each independently adjustable reflective element by activating said mechanical actuators to apply said angular and positional correction factors to reduce an error in said beam angle and said beam position relative to said aperture.

28. A method for detecting a positional beam misalignment and an angular beam misalignment relative to an aperture in an illumination system, comprising the steps of:
  (a) directing light from said aperture along a first light path;
  (b) diverting a portion of light traveling along said first light path to a second light path;
  (c) determining a positional error of the light traveling along the first light path relative to a central axis of said aperture; and
  (d) determining an angular error of the light traveling along the second light path relative to a central axis of said aperture.

29. The method of claim 28, further comprising the steps of:
  (a) focussing light traveling along the first light path to determine the position error from the light that is thus focussed; and
  (b) focusing light traveling along the second light path to determine the angular error from the light that is thus focussed.

30. The method of claim 28, wherein the step of diverting a portion of light traveling along said first light path to a second light path comprises the step of splitting the light traveling along the first light path.

31. The method of claim 28, further comprising the steps of collecting light traveling along the first and second light paths; and focussing the light collected onto a quad cell detector for each of the first and second light paths.

32. A method for detecting a positional light path misalignment and an angular light path misalignment relative to an aperture in an illumination system, and correcting the misalignment, comprising the steps of:
  (a) directing light from the aperture along a first light path;
  (b) diverting a portion of light traveling along the first light path along a second light path;
  (c) determining a positional error of the light traveling along the first light path relative to a central axis of the aperture;
  (d) determining an angular error of the light traveling along the second light path relative to a central axis of said aperture;
  (e) if the angular misalignment is greater than a first predefined threshold, redirecting the light traveling from a source toward the aperture to correct the angular misalignment; and
  (f) if the positional misalignment is greater than a second predefined threshold, further redirecting the light that was redirected to correct the positional misalignment.

33. The method of claim 32, further comprising the steps of:
  (a) focussing light traveling along the first light path to determine the positional error; and
  (b) focussing light traveling along the second light path to determine the angular error.

34. The method of claim 32, wherein the step of diverting comprises the step of diverting substantially one half of the light traveling along said first light path along said second light path.

35. The method of claim 32, wherein each of the steps of detecting light traveling along the first and second light paths comprises the step of detecting the light with a quad cell detector.

36. The method of claim 32, further comprising the step of automating the steps of detecting the angular and positional misalignments.

37. The method of claim 32, further comprising the steps of automating the steps of redirecting the light to correct for the angular and positional misalignments.

38. A method for detecting a positional misalignment and an angular misalignment of light traveling along a path relative to an aperture in an illumination system, and redirecting the light to correct the misalignment, comprising the steps of:
  (a) determining the magnitude of the angular misalignment relative to the aperture;
  (b) determining if the magnitude of the angular misalignment exceeds a predefined angular error limit;
  (c) if the magnitude of the angular misalignment exceeds the predefined angular error limit, determining and executing an adjustment necessary to correct the angular misalignment;

(d) determining the magnitude of the positional misalignment relative to the aperture;

(e) determining if the magnitude of the positional misalignment exceeds a predefined positional error limit; and (f) if the magnitude of the positional misalignment exceeds the predefined positional error limit, then determining and executing an adjustment necessary to correct the positional misalignment.

39. The method of claim 38, further comprising the steps of automating steps (a)–(f).

* * * * *